(12) United States Patent
Heine et al.

(10) Patent No.: US 7,664,604 B1
(45) Date of Patent: Feb. 16, 2010

(54) BREAST CANCER RISK ANALYSIS AND COMPUTER-AIDED DIAGNOSIS

(75) Inventors: John J. Heine, New Port Richey, FL (US); Robert P. Velthuizen, Livingston, NJ (US); Jerry Alan Thomas, Potomac, MD (US)

(73) Assignee: University of South Florida, Tampa, FL (US)

( * ) Notice: Subject to any disclaimer, the term of this patent is extended or adjusted under 35 U.S.C. 154(b) by 211 days.

(21) Appl. No.: 10/065,929

(22) Filed: Dec. 2, 2002

Related U.S. Application Data

(60) Provisional application No. 60/334,643, filed on Nov. 30, 2001.

(51) Int. Cl.
*G01N 33/48* (2006.01)
(52) U.S. Cl. ...................................... 702/19
(58) Field of Classification Search .................. 702/19; 382/128, 132
See application file for complete search history.

(56) References Cited

U.S. PATENT DOCUMENTS

| | | | |
|---|---|---|---|
| 5,133,020 A * | 7/1992 | Giger et al. ................. | 382/128 |
| 5,828,774 A | 10/1998 | Wang | |
| 5,838,815 A | 11/1998 | Gur et al. | |
| 5,854,851 A | 12/1998 | Bamberger et al. | |
| 5,872,859 A | 2/1999 | Gur et al. | |
| 5,970,164 A | 10/1999 | Bamberger | |
| 6,011,862 A | 1/2000 | Doi et al. | |
| 6,067,372 A | 5/2000 | Gur et al. | |
| 6,075,879 A | 6/2000 | Roehrig et al. | |
| 6,091,841 A | 7/2000 | Rogers et al. | |
| 6,115,488 A | 9/2000 | Rogers et al. | |
| 6,137,898 A | 10/2000 | Broussard et al. | |
| 6,167,146 A | 12/2000 | Rogers et al. | |
| 6,198,838 B1 | 3/2001 | Roehrig et al. | |
| 6,205,236 B1 | 3/2001 | Rogers et al. | |
| 6,263,092 B1 | 7/2001 | Roehrig et al. | |
| 6,266,435 B1 * | 7/2001 | Wang ......................... | 382/132 |
| 6,278,793 B1 | 8/2001 | Gur et al. | |
| 6,282,305 B1 * | 8/2001 | Huo et al. .................... | 382/128 |
| 6,301,378 B1 | 10/2001 | Karssemeijer et al. | |
| 6,317,617 B1 | 11/2001 | Gilhuijs et al. | |
| 6,389,157 B2 | 5/2002 | Rogers | |
| 6,463,181 B2 | 10/2002 | Duarte | |

* cited by examiner

*Primary Examiner*—Jerry Lin
(74) *Attorney, Agent, or Firm*—Molly L. Sauter; Smith & Hopen, P.A.

(57) ABSTRACT

The present invention is a method of determining breast cancer risk including the steps of establishing a risk probably value associated with a patient, the risk probability value calculated from an array of risk factors associated with breast cancer, applying a computer algorithm adapted to find abnormalities in the patient's mammogram, and increasing the tolerance level for false positive results in the computer algorithm responsive to a higher probability value associated with the patient and decreasing the tolerance level for false positive results in the computer algorithm responsive to a lower probability value associated with the patient.

13 Claims, 3 Drawing Sheets

Fig. 1

(Equation 1) $$y_0 = c_0 + c_1 x_1 + c_2 x_2 + \ldots c_n x_n$$

(Equation 2) $$P = \frac{\exp(y)}{1 + \exp(y)}$$

(Equation 3) $$\lambda(t) = \frac{f(t)}{1 - F(t)} = \frac{-S'(t)}{S(t)}$$

(Equation 4) $$S(t) = \exp\left(-\int_0^t \lambda(u)\,du\right)$$

(Equation 5) $$\lambda(t) = \int_x \lambda(t \mid x) p(x)\,dx$$

(Equation 6) $$\lambda(t, x) = \lambda_0(t) \exp\left(\sum \beta_i x_i\right)$$

BREAST CANCER RISK ANALYSIS AND COMPUTER-AIDED DIAGNOSIS

CLAIM OF PRIORITY

This application claims priority from U.S. Provisional Patent Application Ser. No. 60/334,643 filed Nov. 30, 2001.

GOVERNMENT SUPPORT

This invention was supported in part by the Department of Health and Human Services, National Cancer Institute, National Institutes of Health, under Grant No. 5 R21 CA79947, and (2) the Naval Medical Research and Development Command funds managed by the Henry M. Jackson Foundation for the Advancement of Military Medicine contract # 600-0675299-169.

BACKGROUND OF INVENTION

1. Field of Invention

This invention relates to systems and methods for analyzing digital mammograms, and, more particularly, to systems and methods for performing a risk analysis and computer-aided diagnosis using digital mammography data.

2. Background

Breast composition, a breast cancer risk factor, is correlated with some of the known risk factors and is independent of others. Understanding these interactions provides a mechanism for measuring the dynamics of breast cancer risk. The present method provides a mechanism for fusing risk analysis with automated computer aided detection in digital mammography.

It has been demonstrated that regular screening by mammography reduces the mortality rate associated with breast cancer (here in "BC"). However, there are debates as to whether the screening benefits are applicable to women of all age groups, and as to when regular screening should begin, sometimes argued at 40 years of age, or more often 50 years of age, since this is where the mortality reductions have been previously observed. However, current research indicates benefits for those that begin regular screening at 40 years of age. Setting this argument aside, it is clear that a serial electronic database will contain many years of clinically normal images for most women, and many years of normal images prior to cancer diagnosis for a small minority of women. The magnitude of this data suggests that reliable automated methods of serial analysis should be useful.

The present invention relates to the risk factors related to the occurrence of BC, examining factors that influence serial tissue change and integrating the associated influences observed in the corresponding breast radiographs. The present invention advances the art in real time automated analysis in digital mammography (DM) with special considerations for serial applications, where risk factors and other patient data are fused with the image data for improved decision making.

Full field digital mammography (FFDM) is a newer imaging technology, where the digital mammogram is acquired directly in electronic format (film-less) as opposed to digitizing screen-film images for processing purposes. This digital system, which is intended to replace traditional film-screen mammography, has the potential to facilitate various teleradiology applications including electronic image archiving and retrieval, remote location analysis, and computer aided diagnosis (CAD) including serial analysis. The disclosure provided herein is applicable to both digitized film-screen images and direct digital images acquired with FFDM systems.

The breast radiograph is a rather crude abstraction of the 3D volume. Incorporating risk information with image measurements brings more information to task when designing CAD methods. The FFMD system allows (as does digitized film-screen images) the direct connection of the digital image data with the other personal patient data (risk factors) in a form that is easily electronically accessible for real time automated applications. Preliminary evidence indicates that in some respects the images are similar with digitized images acquired from screen-film in that cancer detection rates are similar.

A short review of Wolfe's seminal work is helpful. The assertion was put forth that it may be possible to correlate breast patterns with the predilection of BC (this is Wolfe's driving hypothesis). Early on Wolfe observed a relationship between the prominence of ductal patterns and BC in breast radiographs. The associations with lobular tissue (Wolfe referred to this as alveolar tissue), ductal prominence and risk were investigated. Wolfe believed that fat, connective tissue and the epithelial elements are seen as dysplasia (increased radiographic density constituted by interlobular connective tissue) on a mammogram and that periductal fibrosis is represented by prominent ductal patterns. Dysplasia is now an obsolete term, which was used in the past in reference to fibrocystic disease of the breast; for historical reference we use this terminology if the respective authors also used it, which now can be considered in general as increased density. Wolfe made the observation that for normal patients the ductal appearance becomes more prominent in size and frequency with age and decreases with increasing parity, while lobular tissue decreases with age. Similar trends for patients with benign disease were also noted. However, in women with malignant disease, the ductal patterns are more prominent at an earlier age, in addition to having higher proportions of lobular tissue (dense tissue). The correlation of changing tissue patterns with age that Wolfe observed did not take into account the fact that his early images were film mammograms that had higher contrast than the subsequent images that were made with xeroradiography which had a wider exposure latitude that can make dense tissues fade.

Wolfe made the observation that in some cases, even in the absence of a recognizable mass, cancer diagnosis (especially the scirrhous variety with predominantly connective tissue character) might occasionally be made by the appearance of a unilateral group of dilated ducts. In the past the presence of asymmetric breast tissue, especially if increasing in size has been regarded as a mammographic sign of malignancy. The American College of Radiology Breast Imaging Reporting and Data System (BI-RADS) lexicon has defined asymmetric breast tissue relative to the contralateral breast as "a greater volume of breast tissue, greater density of breast tissue, or more prominent ducts. Asymmetric breast tissue has been reported to be depicted on 3% of mammograms and is nearly always benign. Therefore, a stable finding that fulfills the BI-RADS definition seldom warrants a biopsy. Sometimes focal asymmetric densities may represent masses with borders that are ill defined or are obscured by surrounding fibroglandular tissue rather than asymmetric tissue. These need additional evaluation especially if palpable.

In subsequent work the idea of increased cancer risk and ductal pattern was expanded. Wolfe notes that the prominent ductal presence is an abnormality caused by sub-epithelial collagen deposits and that the cross-sectional diameter of the ducts is directly proportional to the amount of collagenosis.

The increased involvement and severity have a very similar age dependency as does breast cancer. A detailed description of ductal image appearance was also provided. Briefly, these are linear bands of increased density that fan out from the subareolar region, and have a discontinuous winding or crossing pattern in a severely involved breast. The presence of cancer alters the duct pattern distribution, resulting in enlarged and winding ducts.

Following this early work, Wolfe developed a detailed classification scheme consisting of four breast patterns that are correlated (this is the driving premise) with BC risk. In this scheme the breast composition is classified by appearance (normally classified by a radiologist's assessment). In ascending relative risk order, the designations are N1, P1, P2, and DY with disregard to abnormalities, vascularity, or any other associated characteristics or risk factors. Here the relative risk means as compared with N1. The N1, normal or negative, is an image comprised primarily of fat with no visible ducts (lowest risk). P1, for prominent duct pattern, low risk, consists primarily of fat with visible ducts occupying up to one-fourth of the volume in the subareolar region (low risk). These ducts appear as cord like or beaded linear structures extending into one quadrant in some cases. P2, the prominent duct pattern, occupies more than one fourth of the volume of the breast and may involve all of the parenchyma in its severe form. DY, the dysplastic pattern, is the fourth category, which poses the highest risk, shows increased density greater than that of fat with absence of a prominent ductal pattern. In this study evidence was presented that the cancer incidence risk progresses with pattern in a significant manner when examining a referral population. It was also noted that not all carcinomas are accompanied by prominent duct patterns suggesting that there may be two types of different age related pathogeneses that indicate risk.

In addition to this grouping, a fifth category, QDY, was added for younger women below the age of 40-45 to account for physiological changes in the breast due to aging. The QDY classification is for women whose radiographically increased density is not as severe; these patterns are the portion of the DY images that are most likely to regress to a low risk pattern with age. In the same work, two studies were presented that corroborate the earlier work in showing a significantly increased cancer incidence for women with high-risk patterns.

Another important observation stemming from this work is related to the changing role of the high-risk patterns with age. Women with the DY patterns account for a large portion of the cancers in the under 50 age group whereas after this age the proportion of breasts with DY pattern is significantly reduced, and women with the P2 patterns account for the larger proportion of cancers, again suggesting the possibility of different agents at play. The age related pattern regression is discussed in more detail in Part 2. The evidence is almost unequivocal in that the high-risk patterns generally regress in time.

In subsequent work, the influence of the aging process on patterns was investigated further by studying a referral population. It was found that women categorized with either low risk or very high risk patterns at initial assessment do not demonstrate much change over time, and that women designated with the QDY pattern sometimes regress to a low risk pattern with age. It was also shown that the patterns change very little for women after the age of 50. In summary it was found the N1 changes to P1 in 14% of the cases, P1 to N in 7% of the cases, DY regressed to P2 in 33% of the cases and to P1 in 11% of the cases, and to N1 in 8% of the cases, and the P2 pattern rarely reverted to another designation. The processes of aging and involution are discussed again with more detail in Part 2.

In later work, Wolfe discusses the elevated incidence risk observed in the P2 and DY patterns and that it is extremely unusual to have a cancer develop in a breast once classified as N1. Wolfe also discusses the time interval, on average about 48 months, between the negative mammogram and histological proof of carcinoma which reinforces the idea that the cancers were not missed at initial screening (this is often termed the masking effect and is discussed in detail below). This work also suggests that true DY (not QDYs) patterns rarely change, and if so revert to P2 patterns; thus the risk does not decrease with time, since the P2 patterns are stable in time.

This early work by Wolfe suggests a significant relationship between the breast composition and risk. Additional support was subsequently provided by Wellings and Wolfe by correlating histological data with breast composition data from 143 biopsies; the highest grades of precancerous epithelial abnormality occurred most often in the combined P2DY group and infrequently in the P1 category and very rarely with the N1 composition. This should be taken with caution, since biopsy material was investigated, which is a priori abnormal tissue. The results may not, in general, be extended to include normal tissue related patterns without further investigation.

There are other methods used to characterize mammographic densities in conjunction with or independently of Wolfe patterns. One more currently used method involves measuring the amount of radiographic densities in the image; that is measuring the tissue that is not associated with fat (radiolucent areas). Another method is the BI-RADS system, but there is little work in the area of relating BI-RADS image classification with risk. For clarity and where appropriate, these methodologies and associated outcomes are addressed separately. For clarity, the Wolfe-pattern risk and density-risk are discussed separately when necessary.

The work presented by Wolfe suggested (a) a measurable risk factor derived from the image, (b) the interval between screening sessions may be adjusted according to breast composition (risk), and (c) screening practice, in general, may be based on parenchymal pattern. This created much debate and early on many attempts were made to duplicate and verify Wolfe's pattern-risk premise. The results of this verification work provide a less than complete picture, since some studies corroborated Wolfe's premise to differing degrees, and yet other research could not demonstrate the association between dense breasts and increased cancer risk to the same degree or not at all. However subsequent analysis, that reexamined some of the earlier pattern-risk work by imposing strict methodological standards, concluded that there is an increased risk associated with dense breasts for women of all ages. Likewise, additional retrospective considerations indicate that carefully conducted epidemiological studies support Wolfe's original assertions. Even though much of this work supports the premise that patterns are related to risk, not all agree that screening can be based on pattern (risk) assessment.

Much of the research supporting Wolfe's original work does so in varying degrees. It is instructive to give a summary of these variations by experimental design. In general there are three classes of studies (a) case-control (CC), (b) cohort (C) and (c) prevalence (P). In the CC study, cases are matched to controls by some criteria (maybe randomly) and compared, which provides Odds Ratios (ORs). Under certain conditions ORs approximate relative risk (RR) estimates derived from cohort studies of the same population. Incidence (cohort) studies allow for true RR estimates, and prevalence studies provide a cross-sectional comparison of those with the disease compared to those without the disease at a particular snapshot in time. CC studies also provide a relative cross-sectional view. First, the pattern-risk assessment is provided.

The earlier prevalence studies (or cross-sectional studies) corroborating the pattern-risk assertion show varying degrees of support when stratified by age and or pattern. A brief synopsis of this work is given in order to provide a full understanding of the variation.

Tabar et al make the important observation that the cancer prevalence rate curve for the N1P1 (that is the combined N1+P1) group for older women resembles that of the younger P2DY (P2+DY) women with an approximate (displacement to the right) 15 year delay. Other reports also show a diminishing risk with increasing age for women with DY patterns. Elsewhere, it has been shown that the P2 pattern may be the highest risk category. Other reports provide evidence, to the contrary, that does not support the pattern-risk premise for prevalence cancers.

Some reports show increased risk for women of all ages with DY patterns and increasing risk with increasing pattern. And yet other research indicates a diminishing risk with age for dense patterns, with one study showing an opposite trend. Some research indicates that the P2 pattern may be the highest risk category. In contrast other evidence indicates an increasing risk for the DY patterns with only a slightly or no elevated risk for P2 patterns, respectively. In comparison, current research involving Singaporean women indicates a high risk associated with a pattern similar to P2 but little risk associated with a classification with DY similar patterns. Other research indicates in general that women in the P2DY group are at an elevated risk compared with the low risk N1P1 group with significantly increased risk associated with the DY pattern compared with the N1, which is in agreement with subsequent work. Evidence suggests that the relationship between high-risk patterns and risk is strengthened when accounting for weight and height. Subsequent to the earlier work, research by Wolfe and other researchers provide general support for the risk-pattern association. One report deserves special attention because it shows an elevated risk for P2DY patterns highest for women in the 45-60 years of age; a study important because the patterns were recorded four years prior to diagnosis. Subsequent reports show slightly elevated BC rates for P2 and DY patterns detected at screening and significantly elevated risks for interval detected cancers within 18 months of a negative screen, and yet other research indicates the pattern-risk assertion holds for postmenopausal women only. Bucchi et al find that women with benign breast disease are more likely to have high risk Wolfe patterns compared with normal women, and have pattern distributions similar to that of women with proliferative and malignant disease.

Some reports do not support the pattern risk premise. Other work shows increased rates for women with dense patterns between 40-54 years of age with the risk falling to unity above this age.

Gravelle et al provide strong evidence for the pattern-risk association with about a 4-fold risk increase for women with P2 and DY patterns. One report demonstrates that when assessing the incidence odds with patterns taken initially, the BC risks are only marginally elevated for the P2 and DY patterns at the end of 8-year screening project. However, when accounting for the longitudinally shifting patterns (assessing the pattern in the screening round preceding diagnosis) the incidence risks are considerably elevated for the high risk group. Although it should be taken into account that this group work tracked women initially between the ages of 40-47 years of age which is the age group that is most likely to experience serial pattern change.

The incidence pattern-risk research also shows considerable variability in risk and associated follow up time. Krook et al show significantly elevated risk for women over 45 for the P2DY group. Research also shows significantly elevated incidence rates for the DY class in a four-year (max) follow-up with only slightly elevated P2 odds associated with older women. On the contrary, other evidence shows elevated incidence rates for both P2 and DY patterns, particularly with the P2 group over a five year interval. de Stavola et al (a hybrid study) show an elevated risk (2 fold) for both pre and post-menopausal women with P2 or DY patterns at the 5 year censoring time, which is in agreement with other research showing increased risk (monotonic increase with pattern) with pattern at the five year follow-up. It is suggested that masking may be in effect since the proportion of stage 1 tumors detected in the P2DY women was less than that of the low risk N1P1 group; this work also shows that by not adjusting for age the incidence risk calculation will be underestimated.

Briefly, the masking effect implies that cancers are sometimes missed in the more dense patterns at initial screening. These missed cancers will then manifest in the near future, which will inflate the incidence risk estimates in the short term. Work by Egan shows an elevated incidence for dense patterns at 36 months with the conclusion that the risk is an artifact of masking. Egan and McSweeney show an elevated risk in the P2DY patterns for up to 48 months, which then falls to unity. This work is interesting in that it gives lead times (time between normal and abnormal reading) for the various patterns, as 43, 44, 33, and 29 months, for the N1, P1, P2, and DY patterns, respectively, and indicates that most (68%) of the developing neoplasms in P2DY breasts occur by the age of 55. Other work that provides little support for the pattern-risk premise include, or for five through nine-year follow-up periods.

Moreover, it is known that the BC incidence rates vary geographically. Asian women are at a lower risk compared with women from the west. Evidence indicates that women from India have a higher incidence of low risk Wolfe patterns compared with Caucasian women, which provides an indirect link with pattern and risk. However, this should be taken with caution. Work based on applying BIRADS tissue compositions indicates Asian women are more likely to have BIRADS 3-4 compositions compared with Caucasians while Native Americans are more likely to have less dense patterns and much lower BC rates compared with Caucasian women. It is the former relation that does not fit well with the incidence rates when considering density as a risk. Although, other research indicates that Japanese women are less than half as likely to have P2 patterns and 4 times more likely to have N1 patterns compared with British women but both groups have similar DY proportions. However, these discrepancies may be due to both the tissue rating system and body morphology. In support of this premise, other research based on quantitative density measurements shows that the mean dense area for Asian women is less than that of Caucasian women, but because of the relatively smaller breast size of Asian women, the associated percent density is larger thus indicating the confounding influence of breast size and density. Research in breast carcinoma among immigrants in Australia and Canada shows a shift towards the rate of the destination country, resulting in the conclusion that environmental and lifestyle factors associated with the new place of residence influenced the incidence of breast carcinoma. An interesting observation was that the rate of incidence and mortality among immigrants took place not only between from low to high-risk countries but also vice versa.

Some researchers have found that relating the amount of radiographic density in the image to risk (density-risk assessment) is a more productive methodology. The loose definition for radiographic density is any image area that is not fat or not radiolucent. Roebuck et al provide a more complete definition for radiographic density. It may be the case that density measurements are a more reliable indicator of risk. The work discussed in this section, for the most part, is cross-section (case control) in nature unless otherwise indicated.

Early work by Boyd et al showed that women with at least 10% dense tissue which he termed dysplastic tissue, were at an elevated risk, and women with at least 75% dense tissue were at significantly increased risk; although, this work shows a weak connection with ductal prominence and risk. The work by Brisson et al is presented in terms of more common radiological terminology when describing densities; in conjunction with applying Wolfe patterns, densities are further classified as nodular and homogeneous (confluent). Brisson et al show that women with P2 patterns have extensive nodular densities while women with DY patterns have extensive homogeneous densities as well as nodular densities, where the nodular densities are smaller and more concentrated in DY patterns. The relation or correlation with density proportions and Wolfe pattern classification is discussed in more detail below. This work indicates some interesting points (a) for women under 60 years of age an increase in the percentage of the breast showing nodular densities is correlated with an increase in BC risk with a similar, but weaker, trend for homogeneous densities, and (b) and increase in the average size or degree of concentration of nodular densities is associated with an increased BC risk. The relation of BC risk with nodular density percentage is strengthened when weight and height are taken in account, and the risk associated with the percentage of the breast showing homogenous densities is not observable until accounting for weight and height. Supporting work shows that the BC risk rises steadily with increasing density percentage. Safitlas et al show that the risk gradient is approximately linear with respect to increasing densities. Byrne et al also show an elevated BC odds with increasing density when adjusting for weight. The evidence indicates the risk holds when considering age. Although, one report shows elevated risks for women with 25% or greater radiographic densities with no trend of increased risk with density after this threshold. Byrne et al also found that with increasing absolute area of the breast with dense tissue increased also shows an increased risk; compared to women with no breast density, women with a total density in cm2: 1-13.9, 14-22.9, 23-33.9, 34-52.9, and 53 or more had odds ratios of 1.48, 1.99, 2.08, 3.24 and 3.35, respectively, which is in agreement with other work. The elevated risks with increasing total density are similar (central values) to those found with density proportions.

Few studies have reported on BC risk and percent density as related to time. One report also suggests increasing density gives significantly elevated risks for 10 years of follow-up. One report using a two class percentage density categorization with a cut-off at 25% density shows an initial elevated risk for the more dense group that increased even further at the 3-4 year interval and then decreased with time, which supports the masking premise (or possibly accelerated tumor growth); although, the masking effect can not explain the initial elevated risk. Brisson et al using a three class density categorization of atrophic (fat), intermediate, and glandular or homogeneously dense, categories show a stable elevated risk for women of glandular and intermediate breast categories of ages 35-49 years at the time of entry. In women who were 50-74 years of age at time of entry, an elevated incidence of breast cancer was observed that diminished with time. A commentary on mammographic densities and related factors is also provided by van Gils.

Some researchers have considered risk, Wolfe classification, and density simultaneously. Byrne et al show that within the P2 and DY patterns, increasing percent densities corresponds with an increased cancer risk referenced to the N1 pattern this research indicates that the raised risk with the high risk the Risk within high risk. Moreover, the work by Byrne et al indicates that within a particular high risk Wofle pattern increasing density accounts for the increased risk. Other work indicates the BC risk is elevated with increasing densities for women with P2 patterns, but shows no elevation with DY patterns with less than 45% densities; however, an increase in risk with density rising above this threshold is observed. The percent density risk relation is further strengthened by research that correlates abnormal histological change with increasing percent density that may indicate an association with high-risk histological changes.

Wolfe Pattern and Density Comparison: only two studies were found that quantify the association of Wolfe pattern with density proportion. Brisson et al split the association (mean values) into percentages of nodular and homogenous densities per Wolfe pattern class: N1, 0% nodular and 0.4% homogenous; P1, 13% nodular and 1.9% homogenous; P2, 45.9% nodular and 3.4% homogeneous; and DY, 24% nodular and 36.7% homogenous. Wolfe et al found that N1 breasts contained less than 0.01% densities, 80% of the P1 breasts contained less than 25% densities indicating some difference in correlation. The work indicates a good degree of correlation for the high-risk patterns in that 98% percent of the P2 breasts contained at least 25% densities, and all DY breasts contained more than 25% densities.

Some research shows BC risk is not related to breast size with or without tissue considerations, or related to total breast area, which is in agreement with other work when considering weight and height. Although to the contrary, work by Kato et al shows a positive association with BC risk and breast area (or volume) for pre-menopausal women, but not for post-menopausal women, where a negative relation (minor) holds while other work shows an inverse relation with risk and size that disappears when considering composition. Yet, research shows an inverse relation with increasing breast size with either high-risk patterns or with increasing density with one report showing an exception for pre-menopausal women with P2 patterns, and that the relation holds for all age groups. Further analysis, when controlling for density, suggests large breasts are normally more fatty and should pose no excess risk, but when large breasts are not fat there is a considerable BC risk. Salminen et al also found that the incidence of favorable serial pattern change is influenced by weight, but the effect is not significant when considering combined influence with weight (BMI), age, and number of pregnancies. In general, evidence suggests that there is little association with BC risk and breast size when pattern is not considered or association between adult height and BC risk.

Related research shows that the total area of the breast strongly correlates with the total non-dense area and much less to the total dense area in pre-menopausal women. The evidence shows that height is associated with total breast area (negatively), area of non-dense tissue (negatively), and percent density (positively) after controlling for weight and other risk factors. These researchers suggest that this correlation work indicates fat and dense areas should be considered separately in etiological studies. Although, this dense non-dense correlation analysis results from studying pre-menopausal women, it may be safe to assume it applies to postmenopausal women also, since menopausal status is not related to breast size. Moreover, other work indicates that breast size is independent of age, parity, age at first birth, or hormone replacement therapy.

One factor in the incidence based risk estimates is that density proportions (or Wolfe patterns) change with time, but it is not clear if the BC risk changes accordingly. One report shows that for postmenopausal women that initially have 5-25% densities that regress to less than 5%, the risk also diminishes. However, no clear conclusions can be made as to women with >25% density at the beginning that regressed. Similarly, with the cross-sectional analyses the composition assessment time is an important consideration.

The breast is a heterogeneous composition of adipose tissue, epithelial cells (parenchymal), and fibrous connective tissue (stromal), and most breast cancers arise from the ductal epithelial cells; since fat is translucent, the density is a result of fibrous and epithelial cells. The total density, as opposed to the proportion, that is the true measure of risk. The differing correlations of dense and non-dense tissue with total breast size aids in quantifying the inverse relation of breast size with high-risk pattern, and also provides support for the total-density hypothesis.

The hypothesis that certain tissue types (total) are the foci for cancer development is supported, circumstantially, by work that shows women who have undergone surgical breast reduction, due to breast hypertrophy, have decreasing risk with increasing tissue removal. This association should be taken carefully since the risk relation may be related to the condition. Moreover, subsequent research indicates a significantly reduced BC risk with breast reduction surgery and that the risk reduction is inversely related to the amount of tissue removed, in particular for women over 40 years of age. The total-density hypothesis is also supported by the work that investigated total density and risk. Moreover, the research showing that Japanese women (low risk) have less total density compared with Caucasians (higher risk), while their associated dense proportions are greater renders additional support.

It has been shown that magnetic resonance imaging (MRI) tissue parameters such as water content and transverse relaxation time, denoted as $T_1$, are useful for separating low risk from high risk Wolfe patterns; high risk patterns show more water content and longer $T_1$ relaxation. Likewise, other work in quantifying the association with mammographic density and MR breast imaging parameters also indicates a positive correlation with percent density and water content, and an inverse association with percent density and $T_2$ relaxation; that is the $T_2$ is longer for fat tissue compared with that of fibroglandular tissue. This inverse relation is similar to that found with $T_2$ relaxation and the DY Wolfe pattern. Moreover, other work indicates a positive correlation between density volume proportions obtained from MRI compared with planar projection density proportions measured from standard mammography but with marked differences in tissue distributions particularly for dense breasts. This work indicates that mammography is limited in its ability to accurately assess breast tissue proportions due to differences with the three-dimension volume and associated, reduced in dimension, x-ray projection.

The totality of the work discussed above indicates that density classification is an important factor to take into account when analyzing mammographic images; the proportion of radiographic densities in the image is related to the elevated risk. Some researchers have acknowledged the importance of automated density measurements. Moreover, research shows that the quantitative evaluation of densities by planimetry correlates well with the radiologist's assessment, Similarly, Boyd et al show that, by either the radiologist's estimation or with a computer assisted manual thresholding, more proportions of radiographically dense tissue are associated with a higher risk. This implies that well designed automated methods have the potential for similar performance.

Magnin et al using texture measures and local statistics classify images into four distinct categories of risk with some success and conclude that a-continuous labeling may be a better approach. Caldwell et al apply a fractal measure for image pattern classification and risk assessment resulting in good agreement with the radiologist. Kallergi et al apply a local thresholding technique and region seed growing method (two different methods) with preliminary results for N1 and DY classification. Taylor et al investigated different measures for estimating texture. This work shows that skewness followed by fractal characterization allows the best discrimination between dense and fatty type images among the various metrics investigated, although the skewness distributions of fatty and dense breasts show some degree of overlap. Tahoces et al investigated various metrics including Fourier measures, local-contrast, and gray level distribution analysis for Wolfe pattern classification based on the analysis of a representative region of interest that resulted in reasonable image classification. Byng et al found that combining a global fractal measure with a global skewness figure of merit, based on averaging local measurements, results in better parenchymal density detection as opposed to either figure alone; both measures were found to be correlated with the radiologist assessment. In subsequent work, this method was applied for assessing risk that showed both parameters were significantly related to risk; although, the correlations with the automated density analysis compared with the reader's assessment was less than in previous study. In addition, earlier work by Byng et al applied a computer assisted thresholding technique for pattern analysis. Karssemeijer applies a KNN classifier based on features found by transforming the data into regions with equal distances to the breast skin line. Huo et al show that women with dense breasts who have a genetic BC predisposition that are at a high risk in accord with the Gail model can be detected with texture measures. Heine and Velthuizen show that a rigorous parametric statistical analysis allows the continuous labeling of dense and non-dense tissue following a pre-whitening technique applied to the raw image based on 1/f noise modeling. Sivaramakrishna et al transform the data into a normalized local variance representation for automated density detection based on thresholding.

There is considerable research in investigating the associations of breast tissue patterns (and or density) with the other known BC risk factors. This work may be important for understanding biological mechanisms or hormonal interactions related to BC. The thought behind much of this work is that other risk factors might possibly mediate through breast tissue or that dense tissue is a surrogate for other risk factors. The idea to keep in mind is that if a particular event or action increases the BC risk, then a corresponding increase in density or upward shift in Wolfe pattern may follow. On the other hand, if some interaction is assumed to reduce risk there may be a corresponding density decrease or downward shift in Wolfe pattern. Indeed, this dynamic appears to be at least partially correct, as discussed below and in Part 2, which may provide a measurable metric for assessing dynamic risk behavior.

The present invention accounts for risk factors that act independently (or not correlated to a high degree) of the tissue characteristics as well as those that are partially correlated with tissue. These factors will be used to incorporate risk analysis into the automated detection methods. From an information theory vantage point, independent factors bring more to the decision making power. Since the density measurement follows from the image analysis, the identification of other factors that are not correlated with density is of prime importance to the analysis.

Often univariate and or multivariate methods are employed to study risk factor iterations. The former assess the relationship of the event (tissue characteristic) with the risk (the variate) singularly. The latter is a stronger approach in the sense that the interactions between the variates are also assessed in relation to the event.

Evidence indicates that nulliparity (positively), parity, or multiparity (negatively) and late age of first child birth (positively) are associated with the incidence of high risk breast patterns. Many of the reports indicate that with increasing parity there is an associated decrease in the likelihood of high-risk patterns. For clarity, it is convention to refer to the N1 and P1 patterns as low risk and the P2 or DY patterns as high risk regardless of the experimental outcome. This convention is followed here where appropriate.

Many of the univariate studies (or similar type analyses) indicate, to some degree, that later age of first birth is related to higher prevalence of high-risk patterns with some reports showing a weak trend. Early age at first birth is an important determinant for the development of favorable breast patterns and this influence may remain life-long. Bergkvist et al noted an increase from 10.8% in the proportion of women with P2 or DY patterns with age of first birth at 21 compared with 18.7% at 30 years of age at first birth and 31.3% among nulliparous women. These effects were marked among oldest women. However, other multivariate work indicates that the association with age of first birth is not significant when controlling for parity.

Similarly, multivariate analyses show that later age at first birth is associated with high-risk patterns, and parity is related to less dense or low risk patterns with the two factors having independent influences with parity having the greater effect. Bartow et al observed a significant association between radiolucent patterns and parous states with OR of 2.75 for parous women. Similarly, Gram et al found nulliparous women are more than 2 times more likley to have high-risk patterns compared with women who gave first birth in their teens, and determined that a multipara women with >4 children are 90% less likely than a nullipara women to have high-risk patterns. It is interesting to note evidence suggests the magnitude in shift from high to low risk pattern from nulliparity to parity is of the same magnitude as the shift from one pregnancy to the next. Gravelle et al found, among nulliparous women, that only ⅓ displayed the N1 pattern whereas the N1 pattern was three times more likely among parous women. Similarly, de Stavola et al show that parous women are about 30-35% less likely to have P2 or DY patterns respectively, relative to nulliparous women, which holds for both pre and post menopausal women. In addition to showing that parity is related to low risk patterns, regression analysis suggests that the shift from high to low risk pattern due to parity is primarily due to the loss of P2 patterns with the shift to P1 or N1 without preference. This work also suggests that the P2 patterns decrease with increasing pregnancies with no further effect on the DY patterns when considering 1-5 pregnancies.

The connections with density proportions are somewhat similar. Brisson et al show some interesting associations (a) increasing number of full term pregnancies is associated with a decrease in nodular densities with little variation due to menopausal status, (b) a similar trend in the mean percentage of breast showing homogeneous densities was shown for pre-menopausal women only, and (c) no trend was apparent for the age of first birth for either density and some association with family history and density (both types) was indicated for pre-menopausal women. Using multivariate analysis Saftlas et al show that percentage of densities decreases with increasing parity. Boyd et al compared normal women with 25% densities with women that have 75% or more densities and found that women with increased radiographic density are more often nulliparous. One report indicates that the combined effects of nulliparity and density act in synergism indicating that density is more than a surrogate for nulliparous status. This work shows parous women with 5-25%, and >25% density are at about a 2.7 and 3.6 RR of BC, respectively, and nulliparous women with >5% density have about a 7 fold increase of BC relative to parous women with <5% density.

Menstrual Factors: An association with the age at menopause was also made by Gram et al indicating that menopause between the ages of 45-52 was associated with a 30% likelihood of high-risk patterns, and a 50% likelihood of high-risk patterns if age of menopause was 52 years or older compared with menopause below 45 years of age.

Generally, the evidence relating age of menarche with pattern is ambiguous. Gram et al show that increasing age of menarche (16 years or more) results in double the likelihood of having high-risk patterns for pre-menopausal women, whereas an inverse relationship was found for postmenopausal women who were 80% more likely to have a less dense pattern if their age at menarche was later (past 16 years). Similarly, later age at menarche was found to be associated with dense Wolfe patterns in univariate analysis, which to the contrary only held slightly for postmenopausal women in a multivariate work with adiposity explaining the effect in pre-menopausal women. The relationship of early age of menarche and low risk pattern is supported by earlier work, although menopausal status was not considered. Yet, other work finds no connection with age of menarche with pattern. Other work provides a clearer interpretation of menstrual history by using the variable years of menstruation and found that the odds of breast cancer increased steadily with the number of years of menstruation. Estimates indicate the odds for developing breast cancer nearly doubled, somewhat linearly, when the number of years of menstruation increased from <25 to >40 years.

Reproductive factors such as parity, age of menarche, age of menopause, and length of the reproductive years have been related to BC risk in that, later age of menarche, early age of menopause, either natural or surgically induced, and parity provide protective effects against BC. A significant inverse relationship with age at menarche and BC risk in pre-menopausal women has been noted with decreased BC risk associated with a menarche age of 15 years or more compared to menarche at age 12 and 13, respectively; the reported reduced risk indicates ORs of about 0.45 for nulliparous pre-menopausal women and 0.72 for pre-menopausal women (without regard to parity) with a weak risk reduction for postmenopausal women (without regard to parity). This does not appear to fit well when compared with the age of menarche tissue relations discussed above. To the contrary, evidence (without regard to pattern) shows increased BC risk with later age at menopause with an OR of about 1.91 among nulliparous women with menopause age of 53 and greater compared with those of menopausal age of <45 years, which does agree with the age of menopause tissue relations discussed above.

The parity-risk relation may help explain some of the conflicting reproductive-pattern associations. Research, comparing uniparous and nulliparous women, suggests that early childbirth provides a protective effect for all periods after birth, whereas late age of first birth induces a higher risk immediately after birth that declines with time.

The associations of height, weight, and body build with pattern risk analysis operate in opposition since tall thin women are more apt to have dense patterns or more percentage density, whereas short heavier women are more apt to have low risk patterns. Two reports demonstrate that the BC risk associated with weight is not apparent unless parenchymal pattern is taken in account, and when considered height is no longer important. Brisson et al found that the proportion of women with P2DY patterns was 93.6% among tall and thin women (height >165 cm, weight <55 kg) and 18.8% among shorter and heavier women (height <155 cm, weight >75 kg)(57). This is in agreement with subsequent research relating BIRADS classification and BC risk indicating risk due to density and increasing weight should be considered independently. Some reports use normalized weight-height relations such as body mass index (BMI) or Quetelet"s index (QI). In general most studies indicate that women with high-risk patterns or increasing densities are more apt to have a lean body build.

Earlier work by Gravelle et al indicate no relation of height with pattern, but when stratifying by menopausal status show the pattern-weight relationship is significant for postmenopausal women with marginal significance for pre-menopausal women. Other work supports the lack of association of pattern-height. Brisson et al indicate with increasing weight there is a considerable reduction in high-risk patterns for all height categories, but the inverse height association (when controlling for weight) is somewhat weaker and not as regular, although visible. Similarly, other research finds no dependency on height and pattern. Other work shows that when controlling for height, heavier women are more apt to have less dense patterns, and when controlling for weight, taller women are more apt to have dense patterns. Kaaks et al found none of the anthropometric variables (height, weight, BMI or hip circumference) to be significantly associated with BC risk in both pre and post menopausal women in work that did not consider tissue characteristics; however, a positive association of BC risk associated with waist to hip ratio was observed (RR of 2.79). Similarly, other work (without regard to pattern) found no association between BC risk and height. Brisson et al shows the percentage of the breast showing nodular or homogenous densities is associated with height and weight (positively and negatively respectively); a similar trend holds good for homogenous densities with respect to weight but varies little with respect to height. Grove et al found women with more dense patterns often have lighter body build with or without adjustments for height. The weight-pattern association is also supported by a study of autopsy data showing that obesity and breast size are good predictors of radiolucent patterns. Longitudinal analysis suggests not only are women with low risk patterns more likely to be heavier (large BMI), women with high risk patterns that are heavier (large BMI) are more likely to experience a favorable pattern change in time. Boyd et al show women with increased radiographic density have significantly higher levels of high-density lipoprotein after adjusting for confounding effects, and conclude that differences in fat metabolism exist between women with and without increased density.

Obesity during the pre-menopausal years reduces BC risk due to an associated reduction of progesterone. This protective effect diminishes after menopause and gradually reverses to increased risk due to bio-available estrogens.

Family history (FH) is a known risk factor for breast cancer. As stated previously, for incorporating risk factors with tissue analysis, serial or non-time dependent risk modeling, and CAD nearly uncorrelated (or more strongly independent) factors of risk bring more power to the decision making process.

A case control study suggests a similarity in parenchymal patterns in twins, more prevalent in monozygotic than dizygotic, implying a familial or genetic influence on patterns. This is supported by subsequent genetic segregation analysis that studied women with FH, where a significant correlation in sister-sister breast density was found when controlling for (or not) many other risk factors, although no significance in the mother-daughter densities was found.

Research that compared normal women with family history to normal women without history shows no difference in patterns. Berkvist et al show, with univariate analysis stratified by age or with multivariate analysis, there is no significant relation with Wolfe patterns and FH, which is in agreement with subsequent research. Boyd et al found a weak association (univariate analysis) with FH and increased density, and when considering FH and parity in joint analysis found a weak relation, which agrees with subsequent research. Similarly, other researchers found a weak association with FH and Wolfe patterns with univariate analysis. In subsequent work, it was shown that women with both FH and with greater density proportions are at a significantly increased BC risk compared to the elevated risk of FH alone. Saftlas et al also found that the combination (greater than the sum) of high risk Wolfe pattern with FH exceeds the risk of either effect individually and conclude the two are independent influences on risk. This work also shows that women with N1 patterns without FH are at minimal (no risk) BC risk. Brisson et al show adjusting for FH (among other risk factors) has little effect of the risk estimates associated with parenchymal pattern. Subsequent work shows the means of homogenous and nodular densities are not associated with FH in postmenopausal women, and are weakly associated in pre-menopausal women. Moreover, other evidence also shows that the risks due to FH and mammographic pattern are additive indicating (a) that they are nearly independent, and (b) the etiologic role of the two are not closely linked. Women with FH had a relative risk of 1.43 for BC compared to women with no family history of BC while women with high risk patterns and FH of are at a relative risk of 4.4 for BC compared to women with N1 patterns and no FH of BC. Byrne et al also found the risk due to FH and mammographic density or Wolfe patterns are independent which agrees with earlier work.

Other researchers also found a general lack of association between FH and pattern with multivariate methods. However, one report, that investigated the association with mammographic density and FH in Japanese women, among other factors with multivariate analysis, indicates an association with dense area and FH. Other univariate analyses (or similar methods) find little, or no, association with pattern and FH, and yet others do find some associations. Wolfe et al also found some relation between pattern and FH in a matched case control study. The conclusion drawn from this work is that FH and mammographic attributes are practically independent sources of BC risk.

Understanding the corresponding correlation of breast composition with histological features as observed from radiographs are important pieces of the pattern-risk premise;

this is particularly true when considering that women with biopsy-proven benign breast disease show an increased risk for subsequent invasive cancer associated with proliferative (epithelial) disorders as compared with non-proliferative disease (fibrosis)(139). Early work by Wellings and Wolfe shows a considerable association with histological findings and pattern (a) the low risk pattern lacks nodularity, linear densities, or confluent densities, (b) the P1 pattern shows increased periductal and perilobular fibrosis that is probably related to linear densities, where the intralobular connective tissue and heavily collagenized extralobular connective tissue are seen in normal lobules, (c) the P2 pattern shows increased fibrosis, atypical lobules, and moderate atypical hyperplasia, and (d) the DY pattern shows marked fibrosis that is more homogenous than the P1 or P2 patterns. To a lesser degree, other work shows some correlation with pattern and histology where lobular epithelial hyperplasia and ductal papillary hyperplasia are associated with the P2 pattern. This is supported by other work based on autopsy data indicating, when stratifying by age for women over 50 years of age (only), there are significant associations with high risk patterns and marked intraductal hyperplasia and micro-calcification of the terminal duct lobular epithelium.

However, earlier research found little (no) association with Wolfe pattern and histological findings that indicates the histogenesis of mammary response is not related to epithelial alteration in the ductal system. Similarly, other evidence indicates no association with histological finding and breast pattern, where the variation in Wolfe patterns is attributable to the ratio of fibrous to adipose tissue with no relation to the amount of epithelial content.

Research based on the percentage of dense tissue in women 40-49 years of age shows that women with extreme. proportions of density (+75%) are at an elevated risk for cancer in situ, atypia hyperplasia, hyperplasia without atypia, and developing non-proliferative disease indicating a connection with high risk histological changes in breast epithelium. Although, this work indicates a lack of association between mammographic density at the biopsy site and histological changes in epithelium that might be explained if mammographic densities are caused by changes in the breast stroma and not epithelium. This suggests that collagen is the histological feature related to breast density detected by radiography that is in agreement with earlier work. As expressed in a commentary given by Feig, although dense breast represents large amounts of fibroglandular tissue, it is not clear if this tissue is predominantly epithelial or fibrotic.

As discussed by Madigan et al, roughly 40 of the breast cancers in the U.S. are attributable to the known BC risk factors, which was investigated without considering density. It would appear plausible to include a tissue related metric in the risk analysis.

The ambiguous nature with age of menarche is in agreement with earlier work in developing a comprehensive multivariate model for BC risk prediction that includes Wolfe pattern risk. This work indicates that the contribution due to age of menopause is significant but difficult to interpret, age of menarche has a relatively small influence, and that menstrual history is better represented as years of menstruation as noted earlier. In the comprehensive risk model developed by Whitehead et al Wolfe pattern, age of first birth, nulliparity, family history (BC in mother), history of benign biopsy, log(weight−100), a surrogate for weight, and years of menstruation were all found to add significantly to the predictive power of the model. The work showed that the interactions with pattern and the other factors in the model were not significant indicating each factor is a distinct source of risk. In subsequent work the non-interaction of pattern with the other factors was verified; adjusting for differences in the non-mammographic factors produced only trivial changes in the BC risk due to patterns, indicating pattern is an independent risk factor. Other research supports the length of reproductive years as a BC risk when controlling for mammographic density in addition to other risk factors such as age at first birth, history of biopsy, education, and family history. This work also indicates that (besides weight) adjusting for the other factors changes the magnitude in the risk with respect to Wolfe pattern or percentage of densities very little, again indicating distinct sources or risk. However, earlier work in developing a multivariate BC risk model, where pattern was not considered, found that age of menarche, family history, age at first birth, and log (etiocholanolone excretion) added to the predictive powers on the incidence model while breast feeding, parity and personal history of breast disease did not contribute. Likewise other work that investigated the joint effects of reproductive factors and body shape suggests the protective effects of late menarche and early first birth are greater for pre-menopausal women and both nulliparous and lean women are more apt to experience a protective effect due to early menopause. Other work also suggests different menopausal status related risks for in situ cancer as related to BMI.

The Gail model which includes age at menarche, age at first live birth, number of previous biopsies, and number of first degree relatives with BC but not pattern or tissue related measures, can also be applied to predict the BC risk over some specified interval. More recently, validation research of the Gail model indicates that the method can predict the number of cases in a specific risk stratum but has less discriminating power on the individual level prediction.

The degree of mammographic density is most likely related to the amounts of epithelial cells or tissue in the breast, and if the initiation of cancer is a stochastic event, the more cells at risk, the greater the potential for BC incidence, which supports the total density area approach, which is supported by the breast reduction work. This also suggests that both ipsilateral views should be considered when assessing risk. It is very easy to conceive of a geometric figure that is dense in one projection and not in the other (for instance a disk). Moreover, maybe it is the density acquired from all four views, combined in some fashion, that provides a more accurate risk measure.

There are degrees of density (due to the extended volume) that are as important as the binary measure, and the degree of density (in some crude fashion is related to the volume) may be a preferred figure of merit for risk assessment as opposed to the dichotomous density labeling. For example, within one image an extremely bright area may correspond to densities that extend throughout the breast volume to a greater degree (more x-ray blocking ability) as compared with another area that is half as bright, but not fat. A texture measure may be deployed in addition to the amounts of density in order to enhance the discrimination of the associated risk since the P2 (nodular densities) and DY (homogenous densities) breasts appear to behave in differently.

The present invention includes methods of modeling mammograms with parametric statistical methods as well as non and semi parametric methods. This advancement in the art is based on multi-resolution wavelet analysis, spectral characterization, and fractal modeling. The present invention includes a risk model based on parameters that are not correlated with density measurements as well as those that are partially correlated with tissue metrics in conjunction with density metrics. The invention (a) incorporates this model into the CAD detection methods, in particular for variable threshold adjustments, (b) segregating images out of the processing pool that do need to be machine processed which may have a profound impact on detection FP rates when the (CAD) algorithms are applied to high risk images only, and (c) develops a comprehensive risk model to aid the mammographer's decision process that includes measurable image factors such as density as well as other risk factors. The evidence indicates that a starting place for this analysis will include FH, length of reproductive years, and a binary variable for parity, in addition to density measurements. The modeling will include making assessments of risk today for a particular subject without regard to the past as well as considering compounding risk over time as in the Gail approach: that is, assessing the absolute risk of breast cancer over some specified time interval.

Aging in itself is a risk factor. This follows from noting that the breast cancer incidence curve is an increasing function of age. Even though the incidence risk is an increasing function of age, the rate of change slows (still positive) after the age of 50 indicating that breast cancer is hormonal in nature, since 50 is roughly the average age of menopause, which is discussed in more detail below. The inference from this is that breast density (or pattern) will shift to a lesser degree (tracking risk) with age as Wolfe noted early on.

Here the longitudinal tissue pattern change is discussed. Among the various reports there is almost uniform consensus that the pattern distributions have a tendency to regress from high risk to low risk with age. Additional evidence, obtained from autopsy data of non-selected non-referred women between the ages of 15 and 98, indicates that age and post-menopausal status are very strong predictors of radiolucency. However, one report shows little difference in density (average measurements) in a cohort stratified at 50 years of age, although with considerable variation.

There is considerable variation in this analysis, and the interpretation of the data must be taken carefully. For instance, cross-sectional (or case control) studies stratified by age give a static view of the pattern distribution. The inference drawn from the cross-sectional work is that the time evolution of the breast tissue is the mechanism driving the age related distribution. A stronger method for determining temporal pattern change is derived from the serial studies that track a group of women over extended time intervals with initial and final mammography assessments.

In general, the cross-sectional work demonstrates that there is a considerable tendency for the more dense patterns to regress to less dense patterns with the DY proportion showing significant shifts with increasing age with regression occurring within the DY group. Other work, to varying degrees, shows similar trends in decreasing dense patterns with age. The average age for women with P2DY patterns is about 53 years, and about 58 for the low risk N1P1 group. Stomper et al show a progressive decrease in percentage density with age, where 39% of the women in the 25-29 age group have 90% or greater density, whereas 76% of the women in the 75-79 age group have predominately fatty type patterns with only 6% of the women having 90% or greater density.

When stratifying the age analysis by type of density and menopausal status it appears that homogenous densities and nodular densities behave differently. The mean percentage of the breast showing nodular densities decreases with age regardless of menopausal status whereas the mean percentage of the breast showing homogenous densities decreases sharply with age for pre-menopausal women only and then stabilizes. In subsequent work Brisson et al verify the dense tissue reduction with age and show that for all age groups postmenopausal women have less dense tissue. Likewise, multivariate work shows that age has an opposite effect on pre- and post menopausal women in that pre-menopausal women age 40 and above have twice the risk compared with women under age 36 while post menopausal women over age 55 have half the risk of postmenopausal women aged under 51 years of having P2DY patterns. This is supported by research suggesting the P2 pattern is more common in older (or post menopausal) women or younger (pre-menopausal) women. Inferences drawn from earlier work by Grove et al implied menopausal status was more important for predicting pattern than age. However subsequent work weakly confirmed this association.

Only a few studies have examined the serial pattern change with longitudinal analysis. One report, which tracked the subjects over a mean interval of 15 years, indicates important points (a) the DY pattern regresses to N1, P1, and P2 (in ascending frequency) at mean ages of 55, 57, and 42, respectively, and (b) small percentages of the P2 patterns regress to P1 (only), with the proportions of P2 increasing with time, and (c) the P1 patterns show no change and (d) a considerable proportion of the N1 breasts progress to P1 such that the N1 patterns show a small decrease over time. Similarly, other work shows (12 year interval) the largest regression from dense parenchyma occurs in cohorts aged 45-54 years and 35-44 years of age. Although the research shows that the proportions of P2 patterns are somewhat stable over many age groups, there is a considerable change in patterns that were originally designated as P2 to less dense patterns, and the P1 shows dynamic behavior in both directions over all age groups. This is consistent with earlier work indicating the P2 patterns are relatively stable in time (7 year interval), although some do regress to less dense patterns. This work also divides the DY group into three subgroups of increasing density and indicates considerable regression within the DY group associated with the most dense DY patterns; about one third of the P2DY patterns regress to a less dense state. Salimen et al also show a considerable number of P2 and DY patterns changing in time (8 year follow-up) with women in the 45-53 age group almost twice as likely to regress as compared with women 40-44 years of age.

For all practical purposes, the reports indicate that the high-risk patterns regress with age. Since the commencement age for screening is often between 40 and 50 years of age it is difficult to describe this dynamic process with great precision. It should be understood that the evidence presented here indicates no clear lines of demarcation such as age of menopause or some particular chronological age where the patterns change abruptly; any apparent boundaries are an artifact of the grouping or study design. This work indicates that any attempt to successfully apply automated change detection (serial analysis) to digital mammograms will have to cope with time-changing densities, which for the most part are normal occurrences. This is in contrast to the often-stated problem that differing x-ray projections associated with the temporal views are an obstacle for serial analysis that must be accounted for prior to analysis.

Involution is the aging process of the breast, where by the functioning elements are replaced by fat. There are relatively few studies that address this mechanism directly, even though the results presented in the previous section are due to involution effects. This process, which begins many years prior to menopause, can be characterized in two stages (a) pre-climactic characterized by moderate atrophy of the glandular epithelium and a decrease in the amount of lobular and acinar tissue, and (b) the menopausal stage, characterized by a progressive loss of all glandular tissue accompanied by proportional increase of fat and connective tissue. It is thought that this process is hormone-related. Related work, where mammary glands were collected at necropsy from non referred women, shows (a) the proportion of epithelial tissue in the breast is a maximum in the third decade of life (pre-menopausal), which decreases afterwards, (b) the average lobule volume decreases with age, while the lobule volume proportion of epithelial tissues increases until around 50 years of age, and (c) the fibrous tissue volume proportion declines until about 50 with the trends in these tissue types reversing after this.

The breast cancer incidence vs. age curve (age specific incidence rates) increases with age, but has an inflection point at about 50 years of age, where the increase slows (but still is positive) appreciably with older age. This curve is consistent with the hypothesis that the loss of glandular tissue leads to a reduction of risk; that is the risk is still increasing but the increase has a slower rate of change. This plot consists of two linear segments with differing slopes that interact at around 50 years of age (about the average age of menopause). For most (non hormonal related) cancers there is a linear log-log relation in the incidence curve (without the kink). This, taken in conjunction with certain BC risk factors, may indicate that breast tissue does not age in the conventional manner instep with the calendar.

The rate of involution may be the true variable associated with risk. The associations of BC with hormonal interactions and involution are suggested by the connection with high and low risk patterns. Oophorectomy appears to have a protective effect against BC that may be due to artificially induced involution, whereas early menarche seems to contribute to enhanced risk. Likewise, late pregnancy, which is associated with the prevalence of dense patterns, can be considered delaying the involution process; thus increasing the risk for BC due to the attendant increased proliferation in the ductal-lobular alveolar system. This suggests that factors that inhibit involution or induce an extended life span of the functional elements in the breast at older age may contribute to increased risk. However, there is evidence that indicates the amount of epithelial tissue in the breast and number of pregnancies is not related. Similarly, a discussion related to aging and breast development provided by Russo et al indicates that the initiation of cancer requires the interaction of a carcinogen with an undifferentiated and highly proliferating mammary epithelial. These authors also discuss pregnancy and how the post partum breast contains more glandular tissue than if the pregnancy never occurred.

The concept of early involution providing some protective affect from BC is supported by work showing that Native Americans shift to less dense patterns at an earlier age compared with Caucasian women, and are also at reduced risk of BC compared with Caucasian women. Likewise, as discussed below, other influences such as HRT may delay involution, and thus induce an additional risk.

Involution may not necessarily occur uniformly across the breast. The related histopathological description is provided in detail elsewhere. Roebuck et al provides another pattern classification, which parallels Wolfe"s work, that considers dysplasia (density) and prominent duct opacities as shadowing artifacts on the normal breast structure. This classification accounts for severity, extent, activity, and accommodates ageing. This study discusses how the involution process affects the classification and appearance of the breast, and that P (related to ductal components) or D (related to dysplasia) shadowing can only be considered normal in areas where glandular tissue remains. Roebuck et al also state that once P shadowing has become established, no reduction with time occurs, although it may become more pronounced with age.

Russo et al discuss lobular development (three types of lobs), and transitions from one to the next. This work indicates (a) nulliparous breast parenchyma is made up of undifferentiated structures such as terminal ducts and lob 1, which remain the predominant structure, whereas (b) history of full term pregnancy correlates with an increase of lob 3 (the proportions of lob 3 are significantly lower since they are occasionally seen). These researchers also indicate that (a) lob 2 is present in early years but sharply decreases after 23 years of age, (b) menopause shows an increase of lob 1 and associated decreases in lob 2 and lob 3, (c) at the end of the fifth decade the breasts of nulliparous and parous women are primarily composed of lob 1, and put forth an interesting premise: the endocrinological and physiological changes triggered by pregnancy in prior years might have imprinted permanent biological and or genomic changes in the breast that may impact the BC development potential even though they might not be manifested at a morphological level.

Ductal carcinoma is the most frequent breast malignancy and has been identified as originating in the terminal ductal-lobular unit (or lob 1). Likewise, lob 2 has been associated with this malignancy development, but no association with lob 3 and the development of malignancies has been found. Experimentally induced mammary cancer research on tissue derived from reduction mammoplasty surgeries shows in vitro cells derived from lob 1 and lob 2 express more readily, changes that are indicative of neoplastic transformation suggesting that these cells are more susceptible to the transforming effects of genotoxic agents.

These ideas suggest that densities measured in the nulliparous women are not equivalent to densities measured in parous women. This is consistent with work showing the loss of dense patterns due to parity primarily influences the P2 population and that the P2 densities have an extensive nodular component.

The masking effect is an argument used to explain (or better refute) the pattern-risk premise when assessing incidence risk. The thought behind masking is that developing abnormalities are sometimes missed or obscured in dense fibroglandular tissue, resulting in delayed detection. This should (a) decrease the prevalence rates with respect to dense patterns and (b) artificially inflate the incidence risk estimates for dense patterns in the short term because abnormalities missed will manifest shortly thereafter, which would then cause the risk to fall over extended intervals. If masking is in effect, evidence that shows decreased screening sensitivity due to dense breasts, in part, provides corroborating evidence. Similarly, examining the factors associated with missed cancers, which are closely related to sensitivity, should help shed light on this subject. However, there may be confounding effects such as age dependent tumor growth. Rapid growth and missed cancers are closely related through a category of abnormalities termed interval cancers.

There is a considerable amount of research devoted to understanding the characteristics of both missed cancers and closely related interval cancers. Missed cancers are related to sensitivity in that they are major factors associated with reduced screening sensitivity. In some instances missed cancers can be considered as a subset of interval cancers. That is if a cancer is currently diagnosed in between screening visits and observable in retrospect in the previous mammogram, it is considered as a missed cancer due to an error in reading. A missed cancer is also a definition used when a cancer is detected in a current screening mammogram that is also visible in the previous screening image with retrospective analysis.

Interval cancers are cancers that are detected, in some fashion, in between regular screening visits. If the previous screening mammogram, reviewed in retrospect, is negative, the cancer can be considered as either a true interval surfacing cancer or mammographically occult at time of initial screening. In this sense, mammographically occult implies that the tumor was present but under the sensitivity limits of mammography.

Some authors explicitly discuss a class of cancers termed true interval cancers, and yet others regard this same situation as occult cancers. True interval surfacing cancers and occult cancers following the definition above are indistinguishable, and often lumped together. The characteristics of these cancers (true interval surfacing cancers) are important in terms of masking. For instance in the limiting case, if all interval cancers are occult cancers that were present previously but not mammographically observable, and some known proportion of occult cancers occur in dense breasts, the odds ratios in risk analysis can be adjusted to find the limiting risk ratio relative to the less dense patterns. These definitions, as associated with interval cancers also apply in an analogous way for screen detected cases with retrospective image analysis.

Another definition of occult follows from a cancer that is currently detected by means other than with mammography that is not visible in the current mammogram, such as palpable lumps. If these cases show some breast pattern dependency, a circumstantial case can be made for masking, since it may be safe to assume that these cancers were present before becoming symptomatic and were not visible. These cases are referred to as occult at diagnosis and truly define the lower limits of mammographic sensitivity.

A closely related case is when subtle signs are found in retrospect, which generates another classification (sort of a hybrid interval classification of occult-error and interval developing). Some studies discussed below investigate interval cancers specifically, and other studies investigate previous mammograms of cancers detected presently at regular screening using the same classification as discussed above.

The masking effect is partially supported by the incidence studies that show the long term risk diminishing for the more dense patterns following initially elevated risks. However, there may be other reasons that provide equally valid explanations for the rising and falling risk estimates as discussed below. van Gils et al studied the masking effect and show elevated incidence risk for women with dense breasts (25% density or greater) up to the 3-4 year interval and then decreasing risk in the 5-6 year interval, which could be interpreted as masking to some degree; it is important to note that the density determination was made at the initial screening. Work by Sala et al also show rising and falling incidence rates, where it is suggested that masking and accelerated cancer growth rate influences may be operating in tandem. Whitehead et al provide an argument based on a hypothetical screening program, where it is assumed equal incidence probabilities for P2DY and N1P1 patterns that indicates the masking effect has a minimal influence on inflating the BC risk and does not explain, completely, the elevated risks associated with high risk patterns. This can be understood by considering that masking is always present, and hence the delayed detection in the screening environment is not affected because there is a continuous folding back of cases due to delayed detection.

Sala et al show the risk for interval cancer is higher for women with P2DY patterns, in particular the DY group, compared with screen-detected cancers. Subsequent work indicates that occult cancers occur more frequently in dense breasts and younger women with the two posing a greater risk than either alone, suggesting independent influences. When comparing the subset of invasive ductal cancers, women with P2 and DY patterns are at a significantly elevated risk of having a grade three cancer compared with women with less dense patterns, which may be interpreted as rapid cancer growth. Subsequent work (case control study) by Sala et al indicates the odds of having invasive cancer compared with cancer in situ are higher for women with P2DY patterns, and that these women are more likely to have lymph node involvement. Here again the interpretation is either masking or possibly a dynamic process associated with dense breasts that could be responsible. Similarly, other work shows an increased risk for women with P2 similar patterns is more pronounced for women with poorly differentiated more aggressive grade three cancers. Work by Adler et al also indicates that the number of false negative cases (FN) is almost twice for invasive lobular carcinoma, which is cancer of epithelial in origin compared with ductal carcinoma with FNs found more often in glandular followed by fibrous and then by dense breasts and in younger age groups.

Evidence indicates decreased sensitivity in mammography screening associated with dense patterns, although not unequivocal, which again renders support for the masking hypothesis, although risk assessment is not addressed in this work. Methods used to calculate mammographic sensitivity are discussed elsewhere and in references therein. Work by Bird et al indicates that missed cancers, which include cancers incorrectly diagnosed at reading and cancers visible in previous mammograms, are more likely to occur in dense breasts, in addition to showing cancers that present as developing opacities are also a cause for missed reading. Similarly, other work also shows missed cancers (error in reading) are significantly lower in mammographic density, relative to the surrounding tissue, and often only seen in one of the two views. Kerlikowske et al show that the sensitivity of mammographic screening is highest for women over 50 years of age who have primarily fatty breast density, whereas for women under 50 years of age breast density did not influence sensitivity. Similarly, evidence also shows age related sensitivity measures without regard to pattern, where sensitivity increases with age. Rosenberg et al show that age per se for women over 40 is a minor determinant of sensitivity, but indicates breast density is an important contributor for decreased sensitivity in particular for women 40-50 years of age contrasted with older women. Other work indicates that the poorer sensitivity in younger women may be due to rapid tumor growth, and shows no decreased sensitivity for women 40-50 years of age. Work by Lehman et al indicates that women with extremely dense breasts are almost twice as likely to have a false positive mammogram independent of age. Ma et al show that breast density, smaller tumor size, and lobular histology are independent factors that contribute to the false negative mammogram and indicate that biological factors are the root cause for misreading. Evidence also indicates age-related differences in patients with non-palpable breast carcinomas in a biopsy study of occult tumors, where the majority of tumors were invasive ductal carcinomas with median patient age of 59 years. Women with ductal carcinoma in situ had median age of 50 years whereas women with invasive ductal carcinoma without associated intraductal tumors had median age of 65 years.

Without regard to age or mammographic signs, evidence indicates missed cancers, including screen and interval detected cancers, account for roughly about 12%–30% of the cases. These figures of merit are supported by earlier work that the shows roughly 30% of the missed cancers are due to observer error, and about ⅓ of the missed cases show some subtle signs in retrospect. Yet other work indicates that roughly 57% of the interval cancers are truly interval surfacing. Porter et al indicates that the true interval cancer rate is about 17%. Moreover, there is evidence indicating that interval cancers (all types) are found more often in younger women compared with screen detected cases. A review of some earlier work in this area can be found elsewhere.

With respect to pattern, research comparing missed cancers, occult cancers (interval surfacing), and occult at diagnosis cancers detection indicates that there is little association between the density groups (P1N1 and P2DY) or type of detection category when combining screen detected with interval detected cases. Burrell et al using a slightly different detection classification and studying strictly interval cancers indicate a similar lack of association; however, all the occult at diagnosis cases were found in the P2DY group. This is in agreement with earlier work showing occult at diagnosis cancers were more likely found in women with low QI, and with women with P2DY patterns compared to women with screen-detected or interval detected cancers. This work indicates that about 16% of the interval cases are occult at diagnosis (but included cases with subtle signs), and finds no pattern dependence for missed interval cancers. Similar associations with high risk Wolfe-patterns and occult cases of this nature were also found in earlier work. One report that investigated interval cancers with respect to BI-RADS tissue composition finds women with dense breasts are at a significantly high risk for interval cancer when controlling for other factors compared with screen detected cases, but showed that when stratifying interval cases by age, women between 40-49 years of age with dense breasts were not at an elevated interval risk when compared to women with less dense breasts.

This work indicates that masking due to dense breasts is a factor to consider, but the magnitude is not that great. However, this should be qualified with the understanding that much of the work investigating interval, occult, or missed cancers does not stratify the analysis by pattern and age simultaneously. In addition, the lack of analysis using proportions of density (rather than Wolfe patterns) results in less than a complete picture. One safe assumption is that a well defined incidence-risk study should make adjustments for cases that are missed in the previous mammogram.

The variation in the sensitivity-age relation may be in part due to exogenous hormone use. Evidence indicates that estrogen replacement therapy, in conjunction with increased breast density, are significant factors that contribute to decreased sensitivity in women over 50. Similarly, other research indicates reduced sensitivity and specificity (false positive or FP rate) for women over 50 years of age using estrogen replacement. However one report that studied the effect of HRT in current, previous, or never users indicates no decrease in sensitivity due to HRT with a marginal decrease in specificity. However, other work indicates that women on HRT are almost at twice the risk of experiencing an interval cancer relative to non-users, which is interpreted as a sensitivity decrease.

Cancer dynamics and tumor growth rates are important factors to consider when designing screening systems. These factors may also be related to BC risk and reproductive factors and are discussed below. The time that a particular disease remains in the pre-clinical stage is termed the sojourn time, and is an important time interval to consider when assessing the efficacy of a screening program. Often this is replaced by the mean sojourn time (MST). Likewise, an important related parameter for assessing tumor growth rates is the tumor volume doubling time (DT).

The sojourn time is related to the screening sensitivity and has an influence on screening practice. Assume that a disease is detectable by some imaging modality at time $T0$, but is asymptomatic, and that the disease exhibits symptoms (becomes clinically apparent) at time $T1$, the interval $T1-T0$ is the sojourn time. This is the total time that would have elapsed when the disease could be detected without diagnostic intervention. Now assume that the individual is screened at time $T2(T0<T2<T1)$ with the correct pre-clinical stage diagnoses, the lead time or the time that the disease is brought forward is $T1-T2$; the probability that the diagnosis is correct in this interval is the sensitivity of the test. The sojourn time provides an absolute upper limit to the lead-time obtainable and gives an indication of the effective screening interval. The shorter the sojourn time the shorter the screening interval.

There is considerable evidence indicating tumors progress faster in younger women from the preclinical to clinical phase, implying faster growth rates and shorter sojourn times compared with older women. Other related work indicates similar effects. Using a Markov-chain model to estimate tumor progression rates, research shows shorter sojourn times for women between 40-49 years of age compared with older groups of 50-59, and 60-69 years of age with sojourn estimates of 2.44, 3.70, and 4.17 years, respectively, which is consistent with earlier work. This is also in agreement with earlier work showing similar trends in age dependency lead times. Although, Brekelmans et al provide even shorter age specific sojourn times of one year for the 40-49 age group.

Related research shows that the proportion of tumors capable of dedifferentiation, that is the ability of a tumor to change grade, appears greater for the 40-49 year age group. This is in agreement with work discussed earlier suggesting true interval cancers (aggressive pathologies) are more frequent in younger women, are larger in size, and may be biologically different compared with cancers detected at regular screening. Earlier research also indicates that interval detected cancers may be biologically different from cancers detected at regular screening; that is they are fast growing, and more often found in younger women, which is in agreement with other research. DeGroote et al also suggest interval cancers are a more aggressive form of cancer compared with screen-detected disease. Gilliland et al show that (a) mammography is more likely not to detect cancers with high proportions of proliferating cells (Ki-67), (b) interval cancers have a greater potential for dis-regulation of cell cycle (a potential for genetic instability) as measured by p53 expression when comparing interval with screen-detected cancers, and (c) younger women have higher proportion of rapidly proliferating and aggressive tumors. Similarly, other evidence indicates that the mean sojourn time for women in the 50-69 age group is dependent on the tumor histology, ranging from 2-7 years, whereas women in 40-49 age group show no such histological dependency with a mean time of about two years. Subsequently, Tabar et al discuss the evidence that indicates tumor grade, size, and lymph node involvement progress more rapidly in younger women, which is in agreement with similar research. In contrast, other work also indicates that interval cancers are more likely to emerge in women between 40-49, but shows little evidence of biological aggressiveness.

Other work shows that the tumor volume doubling time is appreciably faster in younger women. It should be clear that both sojourn times and tumor doubling times are slightly different measures, but are closely related approaches. Work, using an exponential growth model approximation, indicates age dependent volume DTs of about 157 days for women between 50-70 years of age and 80 days for women younger than 50. The age related doubling times are similar to those estimated earlier. It is interesting to note that applying the exponential tumor growth model, and assuming malignant growth starting from a single cell, or small cell clusters, suggests most breast cancers start growing around the age of 40. One report indicates no relation between tumor growth rates and Wolfe patterns.

There are three interacting factors that are responsible for the confounding pattern-risk incidence studies (a) younger women are more apt to have dense breasts, (b) evidence indicates that malignancies progress faster in younger women, and (c) mammography is less sensitive to the more dense breasts. There is some research indicating that there may be an association with pattern and cancer dynamics. Ciato et al found an increased prevalence of stage one tumors in the less dense images which is supported by other work showing women with P2 or DY patterns are more likely to have grade three cancer as opposed to women with N1 or P1 patterns that are more likely to have tumors characterized as grade one or grade two.

The term parenchymal density refers to a composite of stromal and epithelial tissue. The evidence indicates that there is some interplay between these constituents, and the stromal content may act as a growth factor reservoir that not only helps promote tissue growth but also plays some regulatory role in cancer growth. The stromal-epithelial growth factor associations and the sex steroidal relation with mammary tissue proliferation are provided elsewhere. Since the evidence indicates that cancer progresses faster in younger women, and younger women are more likely to have dense tissue, it would be reasonable to make the inference that there should be a density dependent tumor growth rate exhibited, particularly in younger women, which would then provide support for the pattern-risk premise. One report in this area, implemented some time ago, with Wolfe pattern analysis that found no association with growth rates and pattern, which is suggested in another report that shows true interval surfacing cancers are not favored in the P2DY combined group.

The conclusion drawn from this survey is that many interactions are at play. If the pattern-risk premise is true, then more tumors will manifest in dense breasts. These tumors are more likely to grow faster and thus influencing the incidence rates in the short term since dense breasts are more common in younger women. It is equally safe to assume, that some abnormalities are masked, most often in dense breasts, which will emerge and artificially inflate the incidence rates, but to a small degree.

A review of the work in HRT and risk given by Jacobs et al indicate HRT use presents an additional BC risk. Moreover, other research in Wolfe pattern risk assessment and HRT use shows that only women with DY patterns on HRT are at a significantly elevated risk, indicating a synergistic risk affect for the combination. The idea here is to understand how this treatment influences the temporal image appearance. Here again there are cross sectional studies as well as incidence studies, where the pattern is assessed prior to therapy and during therapy with the latter giving a dynamic view of tissue change.

In general the cross sectional studies indicate women undergoing HRT treatment are more likely to have more dense patterns with one exception. Likewise one report indicates increased density for women over 55 years of age with no difference for younger age women.

Many of the dynamic (serial change) studies indicate that there is an increase in percent density (proportions of dense tissue) influenced by HRT treatment, with two exceptions that indicate the treatment is not responsible for the increased prevalence of high risk patterns in women on treatment with no shift toward dense Wolfe patterns with the use in cancer patients. Other research indicates that HRT use influences unfavorable change in Wolfe patterns with no impact on favorable change.

The evidence indicates the increasing density shift takes place in the short term of approximately 1-2 years, and the degree of change is dependent on the treatment regimen, with the greater influence due to the combination of estrogen and progesterone rather than estrogen alone. Similar effects were also found with ultrasound analysis, and magnetic resonance imaging work.

Work by Leung et al shows that the change takes place in the short term and that no significant density change was noted at the 5 year mark compared with 18 months.

Work by Kaufman et al suggest that women on HRT for five years or longer experience a delay in the involution process compared to women not on the treatment that show the shift to less dense patterns with age. This idea is supported by subsequent research that shows a significant shift to less dense patterns for non-HRT users when compared with HRT users, where 80% of the users show no shift by 55 years of age. Even though the work by Stern et al shows that a small portion of the women experience interval density increases with treatment, the work suggests that there are significant density decreases in non-users of 55-64 years of age while the density is maintained in users, thus supporting the delayed involution premise. Likewise, a serial DM study also suggests that HRT use delays involution rather than increasing the actual density proportions. The delayed involution observation is consistent with the comparisons of HRT and menstrual cycle breast epithelium morphology discussed above. One study, that investigated BIRADS composition classification indicates that HRT initiators are more likely to increase in density, discontinuers are more likely to decrease in density and continuers are more likely to have increased density, all relative to nonusers with older initiators having a greater risk of increasing density.

Quantitative assessments of the shift indicate that 73% of the cases experience a shift to more density with a mean increase of a little less than 7% with greater shifts for those with less dense baseline measurements; this work also shows a shift in Wolfe patterns from low to high risk in 24% of the cases. Earlier work by McNicholas shows that 27% of the cases showed 10% or greater increases in glandular density. In addition, two specific cases of emerging densities in the short term due to HRT are discussed and shown in detail by Doyle and McLean. More recently, other work shows that only 8% of the women experience a density shift.

Cyrlak et al discuss some of the earlier work in HRT and breast density increase, where a pictorial essay of the influence is provided. The authors discuss the interaction of progesterone with estrogen and how the two act in synergism in the distal portion of the duct favoring differentiation into acini, and promoting lobular growth; and that in diametric opposition, progesterone converts the proliferative effects of estrogen on the ductal cells into cellular differentiation. A cross sectional biopsy analysis of cell proliferation shows that women treated with estrogen and progesterone are associated with greater breast epithelial proliferation and cell density than those treated with estrogen alone, or those with no treatment with the effects localized to the duct-lobular unit. These researchers also indicate that the breast epithelium morphology in the combination treatment is consistent with that observed in mammary tissue during the luteal phase in cycling women and is similar in amount. In related mouse mammary studies evidence indicates the HRT use increases mammary cell proliferation in surgically induced menopausal mice.

As with much of the research in this area, no sure conclusion can be made as to the real influence of HRT. The compensating variables at play are difficult to isolate. The natural aging (decreasing time related density) is most likely different for each woman and the HRT involution retardation and or cell proliferation may be simultaneous constituents for the HRT-density relation.

It is quite reasonable to expect that menstrual timing (MT) would have some impact on the breast tissue, since natural cycles result from hormonal influences. In fact, there is evidence showing MT has an impact on the breast volume size and image appearance.

Magnetic resonance (MR) imaging research shows that there are significant differences in total volume, parenchymal volume, parenchymal water content, and T2 relaxation, but not fat volume or T1, depending on MT, with the parenchymal tissue volume highest in the second half of the cycle, termed the luteal phase. This is consistent with subsequent MR work showing increased water and fibroglandular content in the later menstrual phase.

For reference, the relations with the MR signal and breast tissue in terms of radiolucency are: high water (blood), moderate water (epithelial), low water (connective tissue), and no water (fat). Similarly, work by White et al shows that a smaller proportion of women have extremely dense breasts in the follicular phase (first phase) of their menstrual cycle with the effect more exaggerated for women with a more lean body build.

Evidence suggests that dense mammograms are more difficult to analyse, which is in accordance with work showing significantly increased chance of a FN mammogram assessment when the image is acquired during the luteal phase. A discussion given by Baines suggests that menstrual cycle and the related endogenous hormones may hold the secret of why younger women do not benefit from screening and subsequent therapy.

Menstrual timing is a consideration when acquiring images for automated serial analysis. If possible, the images should be acquired within the same phase and preferably in the follicular phase for pre-menopausal women. In addition, Spatt et al make the observation that if radiation therapy is to induce a carcinogenic mutation it would have to do so when the ductal cells are in the G2 phase, and that there are greater proportions of cells in this condition in the progestational phase (luteal) of the menstrual cycle.

As with other aspects of this analysis there is some evidence that provides counter intuitive view. Research, using mammography in conjunction with urine and blood analysis to investigate endogenous hormone levels during the luteal phase, shows higher levels of estrogen and prolactin and lower levels of progesterone in women with N1 and P1 patterns as compared with the high risk P2 and DY group. The authors suggest that the reverse would be true if endogenous hormones were responsible (causal) for dense tissue.

There are ongoing debates as to whether or not OC use presents as an additional BC risk factor, with many studies finding no association. Recent evidence suggests long-term use is coupled with increased risk for older women.

Earlier univariate analysis shows a high proportion of low risk patterns in women who have used OC (pre-menopausal). In support, subsequent univariate analysis stratified by menopausal status, shows an increase proportion of N1 patterns and a decrease of P2 patterns for pre-menopausal women who have used OC in, although not significant. In is subsequent multivariate analysis this variable was not found important. However, one report indicates no significant association with pattern and OC use in the general population, but when stratifying by menopausal status shows that postmenopausal women who have ever used OC were more likely to have high risk patterns. de Stavola et al, with univariate analysis, show a positive association with OC use and low risk patterns in pre-menopausal women and an inverse association for postmenopausal, but with multivariate analysis the associations were not found significant.

A cursory discussion of the interplay of hormones, age, breast tissue, and general reproductive characteristics might help shed some light on variation in the pattern-risk analysis. This may also provide some insight into developing both well designed studies and experimental approaches to help resolve some of ambiguities involved with the tissue-risk phenomenon. Normal breast development depends on age, breast tissue composition, and past/present hormonal environment. As expressed by Pike et al and borne out in the work by Whitehead et al, the breast age, either defined as starting at menarche, taking in account the distance between menarche and menopause, or the distance between menarche and age at first birth are important time-related factors to consider, as opposed to the chronological breast age as discussed earlier. Boyd et al also provide a similar discussion, premised on this earlier work, indicating that the breast tissue, in some way, may provide the cumulative index of the past and present hormonal interactions. Work by Rockhill et al also provides supporting evidence that the various ways of representing age may interfere with the risk analysis. The point to stress here is that it may be worth exploring methods of normalizing the analysis to account for age of menarche, and perhaps stratifying the analysis according to the distance between menarche and menopause. A good discussion of reproductive history, cell proliferation and breast cancer risk is also provided by Pike et al.

Much of the density related work is an effort to correlate known risk factors with corresponding changes in density (or pattern). If the relationships hold, a mechanism then exists to measure if a particular action influences risk; that is breast tissue in some way may be considered as a biomarker for environmental or hormonal influences. There is evidence indicating that this holds for some important cases not discussed above. A case control study shows significant reduction in the incidence of mammographic density in postmenopausal cancer patients on tamoxifen therapy (a treatment that increases disease free survival rates and mortality for cancer patients). As expected the incidence of high risk patterns with the cancer patients relative to the normal control group shows a significant excess of high risk patterns at the initial screening. However, the high risk patterns of the cancer group regress in time due to therapeutic interaction; the study shows that most change due to treatment occurs during the 10-25 month interval, which is in agreement with earlier work. Similarly, subsequent reports show a density decrease in high risk women on tamoxifen therapy over a two year interval, which is consistent with work by Brisson et al indicating a shift to lesser densities (apparent 1-3 years) primarily for women under 50 years of age. These reports coincide with histological studies of pre-menopausal cancer patients on tamoxifen treatment showing reduced proliferative activity of mammary tissue. Likewise in a study of hormonal contraception that uses gonadotropin agonist in addition to low doses of estrogen and progestron, which attempts to minimize exposing the breast epithelial to these steroids, shows substantial reductions in breast density over a one year follow-up relative to the baseline reading.

In pre-menopausal non-pregnant women, epithelial cells are in a dynamic state undergoing a continuing life and death process due to cyclic ovarian (estrogen-progesterone interaction) function. In these women, the maximum breast epithelial proliferation rate is in the second (luteal) phase of the menstrual cycle, which is also suggested by the MR work discussed previously. This repetitive process increases probability of somatic cell mutation and thus presents a BC risk. This is consistent with the differences in BC incidence curve rate of change in menarche-menopause years compared with the postmenopausal period. It is also interesting to note that the breast cancer incidence rate of change for women who have undergone oophorectomy (artificially induced menopause) below the age of 35 years of age parallels that of postmenopausal women. Although it is important to note that, to the contrary, earlier work shows increased endogenous hormones in the luteal phase, but finds no relation with high risk Wolfe patterns and endogenous hormones.

Other research indicates that breast cell proliferation is similar over OC induced cycles a as with normal menstrual cycles, which is consistent with the risk analysis that shows no elevated risk for younger women using OCs as discussed previously. This is also consistent with the pattern analysis by Leinster and Whithouse that shows no significant difference in the patterns of pre-menopausal women who have or have not used OC. Work by Spicer et al show that when using a reduced estrogen and progesterone OC regimen (reduced to the levels of that found in postmenopausal women) there is an associated serial decrease in mammographic density, where the authors believe the density mirrors reduced risk.

Other evidence indicates the characteristics of breast tissue are determined early in life. Increased placental (the main estrogen producing organ during pregnancy) weight may be a perinatal indicator of high risk pattern. This bodes well with work that addresses the effects of the proliferation of rudimentary breast epithelium and influences due to endogenous hormones and testosterone in fetal development.

The epithelial content decreases with age varying 15%-5% by volume from young to older women, respectively, but the functional form of this decay is not understood, and the relation with what is observed on the radiograph is not clear. Moreover, a case-control study of women with a history of benign breast biopsy shows that age, menopausal status, and years since last birth influence epithelial percentages, whereas oral contraceptive use and body morphology characteristics influence stromal proportions; the work also shows decreasing proportion of epithelial content with age. This analysis was at the biopsy site and may not apply across the breast but does provide circumstantial evidence that the density analysis of mammograms provides a crude scenario of the dynamics at play when used in isolation. Likewise, the work provided by Russo et al also suggests that densities as measured on mammograms are not equal, since the predisposition for BC depends on the lob aggregate, which is dependent on the reproductive history.

A critical epithelial-stromal ratio may be important. Likewise, when assessing density, there may be an age related correction or conversion function that will allow better risk estimates. That is the amount of dense tissue that is at risk may be found by applying an age dependent adjustment to the actual image density measurement. The evidence indicates the epithelial content decreases with time, but may not be resolved in the radiograph since it (the epithelium) is of limited volume to begin with and may be masked by stromal content.

The volume changes during the menstrual cycle noted in the MR work may hold some clue. As reported the parameter changes due to MT vary greatly within each individual. If in some way this change is more closely related to one of the dense constituents than the other, perhaps a better assessment of the true tissue at risk can be made. The research by Bernardes et al shows that tamoxifen has a definite impact on reducing cell proliferation for those on tamoxifen therapy as measured over one menstrual cycle. The research in MT and mammography indicates the changes in mammographic density due to menstrual phase for normal women are observable in standard x-ray images for some cases, although quantitative methods were not applied for image analysis. These changes are consistent with the MR volumetric work discussed above. It is possible that over many menstrual cycles there is a cumulative effect due to tamoxifen therapy, or a similar type therapy, which manifests over extended periods as a decreased density for some women, in particular for lean women.

As pointed out by Hutson et al, mammary carcinoma more often develops in the upper outer quadrant of the mammary gland, but the related analysis shows that the epithelial content is greater in the lower half. This suggests that there may be a spatial aspect of density analysis that has not been considered in the risk analysis as of yet. Density may be a risk that has a spatial dependence. Similarly, other work also shows a spatial dependency in tumor growth. It may be wise to consider this as a spatial risk factor when considering CAD development and explore methods of adjusting parameters dependent on spatial location.

Little research has been aimed at understanding the interplay between diet, and or exercise with serial pattern change. Boyd et al showed that women on a reduced fat diet showed no significant density or dysplastic change after one year. However, subsequent research indicates that the adoption of a reduced fat and increased carbohydrate diet influences radiographic appearance. This work, that followed women initially with greater than 50% dense breast, shows decreases in breast area, primarily accounted for by weight loss, and loss of dense area and percentage area attributed to the intervention diet after two years with the effect more pronounced in women going through menopause. Subsequent work of similar dietary intervention of women going through menopause shows significant reduction in dense area, attributable to changes in cholesterol, total fat, and saturated fat intake, and changes in percentage density, attributable to changes in cholesterol and saturated fat intake, in addition to showing that women with FH of BC show less reduction that those without. Other work shows little or no association with alcohol intake and density proportions. This is consistent with alcohol-risk research that shows no increased risk for alcohol users less than 50 years of age and increased risk for those over 50.

Cross-sectional (case-control) research indicates a positive relation with saturated fat (or total fat) intake, and inverse association with fiber and carotenoid intake with homogeneous or nodular densities, but no regular association with high risk Wolfe pattern. This work also shows no significant relation with pattern and polyunsaturated fat or cholesterol intake. Likewise, subsequent work demonstrates a positive correlation with fat intake and women with DY patterns. However one report indicates increased breast density with decreased intake of saturated fat in pre-menopausal women. Other work indicates an association with protein (post menopausal women), carbohydrate, and meat (post menopausal women) intake with high risk Wolfe patterns and no significant relation with fat or vitamin intake with pattern. In a case-control study of ethnicity and mammographic density evidence indicates an inverse relation with soy intake and breast density.

Only one case-control study was located that addresses physical activity and breast density. When controlling for confounding factors, this work shows a weak inverse association with density and moderate physical activity with the strongest association found in young women in the highest category of activity. The inference could be made that exercise induced morphological changes can influence mammographic patterns through alternative avenues such as breast size and body style as discussed previously.

In general, Hoffman-Goetz et al provide a good review on the association between exercise and BC that includes reproductive, hormonal and endocrine mechanisms. The authors indicate that the evidence suggests an inverse relation with exercise and BC. This is in agreement with other reviews indicating physical activity reduces the BC risk in particular lean, parous and pre-menopausal.

Setting the age-related screening commencement argument aside, the screening pool is at the age where significant proportions of the patterns or densities are most likely to shift, more often to a lesser degree. For robust automated sequential image analysis, these shifts should be understood and incorporated into the analysis scheme. A quantitative measure for "normal" aging associated with density measurements or tissue composition analysis obtained from radiographs has not been researched to any great extent.

Serial image analysis, in many cases, is synonymous with what is generally termed change detection. Change detection has its roots in the (non-medical) image analysis of similar scenes acquired at different times. An intuitive method for finding change, which is productive in many cases, is sequential image subtraction, which may be considered as a time derivative. It follows that large changes result in large signals in the time derivative image. Some applications include the study of scenes acquired from aerial or satellite surveillance. Techniques such as geometric image warping, rigid rotation, and translational alignment (often termed image registration) are sometimes employed to correct for atmospheric interference or for differing inclination angles.

More recently, change detection (serial analysis) applications have found their way into the medical imaging analysis arena with applications in DM. It is often inferred that geometric warping is an important initial correction that should be applied prior to automated analysis methods. This inference is made because it is assumed that serial mammographic images will most likely result from differing x-ray projections due to plate compression and patient positioning, and is probably a true assumption. However, this author does not know of any work that provides a quantitative analysis as to the extent of the problem. The work by Kostelec et al also shows that anomalies results when applying warping techniques to dissimilar regions assumed the same. The constraints or boundary conditions for the warping procedure are that sequences of images (a serial pair) are the same; the serial pair only differs due to the projection-position distortion. The work presented in this review suggests that this is an assumption that is most likely not applicable in many cases. Additional temporal effects must also be accounted for in the sequential image analysis that applies to pre- and post menopausal women separately.

For pre-menopausal women, optimal imaging acquisition should include menstrual timing, since volumes and density characteristics may change. That is for automated analysis, the images should be acquired at the same stage of the menstrual cycle, and if possible during the follicular stage when the breast is less dense. Also OC use is a consideration, but the evidence is not clear as to the influence on the breast image. This may follow from noting that the circulating hormones due to the natural cycles are similar to those during OC use.

For postmenopausal women, the start of HRT therapy should also be considered. From a pragmatic stance, the evidence shows that if a change in mammographic structure takes place, it does so in the short term. The suggestion here is to update the baseline image at about the 24-month mark for women starting this therapy. Likewise, the evidence suggests that discontinuing HRT encourages the commencement of the normal involution process.

Likewise, there are other factors to consider such as weight change, or change in exercise habits, and the general aging in terms of breast density influences. Although limited in scope, the research indicates that body morphology is related to breast tissue, and that a well designed serial analysis should attempt to track this information.

There seem to be distinct sources of error that propagate through pattern-risk analysis (a) the methodology applied to estimate parenchymal characteristics for example Wolfe pattern, BIRADS, or density analysis, (b) the masking effect, (c) possibly age related cancer growth rates, (d) the time at which the pattern was assessed (present, past or some combination of the past with the present), (e) the nature of the tissue at risk, since dense tissue is a composite of epithelial and stromal content, and (f) perhaps there is a spatial dependency for dense tissue and risk.

For the past decade or so many researchers have developed novel approaches for CAD with many methods based on detecting or enhancing the abnormalities. For the most part these methods have been applied to digitized film images. The general definition of CAD is widened in the present invention to include understanding the complicated and entwined factors discussed in this specification. That is, CAD should also include developing methods for quantifying the factors discussed here, in addition to detection, classification, and teleradiology applications. With the advent of real time digital images (the FFDM) system, it may be possible to quantify the temporal influences of involution or aging, HRT, environmental, other hormonal interactions, and the pattern-risk assessment and link these factors with the actual image measurements.

The FFDM data collection system directly supports the serial analysis of involution and time related density change and risk analysis. The automated density analysis methods, discussed above, should permit the real time risk assessment, due to dense tissue, over extended intervals. This should enable the tracking of large cohorts over many years with density measurements made at each screening session for the participants. In this fashion, in conjunction with the radiologist's assessment, more accurate risk assessments relative to density should result.

SUMMARY OF INVENTION

The present invention is a method of determining breast cancer risk including the steps of establishing a risk probably value associated with a patient, the risk probability value calculated from an array of risk factors associated with breast cancer, applying a computer algorithm adapted to find abnormalities in the patient"s mammogram, and increasing the tolerance level for false positive results in the computer algorithm responsive to a higher probability value associated with the patient and decreasing the tolerance level for false positive results in the computer algorithm responsive to a lower probability value associated with the patient.

The risk factors may include relative risk values, odds ratio values or absolute risk values. An advantage of the present invention is its utility in automated screening. Accordingly, an embodiment of the invention includes the steps of obtaining a patient-specific breast tissue density value derived by automated means from the patient"s mammogram and integrating the breast tissue density value in the risk probability value. Mammograms generating a positive result for breast cancer are flagged for additional analysis. A recommended course of action may be automatically generated wherein more invasive procedures are recommended responsive to the higher probability value and less invasive procedures are recommended responsive to the lower probability value.

In another embodiment, a data entry interface adapted to input the array of risk factors associated with the patient is provided and the patient's mammogram is digitally acquired. The array of risk factors is stored on an electronic storage medium communicatively coupled to the digitally acquired mammogram. The algorithm is applied to the mammogram to find abnormalities. Optionally, mammograms associated with abnormal risk findings are electronically presented with computer aided enhancement.

The array of risk factors includes at least one factor selected from a group of factors including age, racial background, geographic background hormonal data, breast size, weight and height, pregnancies, breast surgeries, breast water content, transverse relaxation time, family medical history, previous biopsies, length of reproductive years, menopausal status, parity, age of menarche, age of menopause, involution characterization, density time dependency, density dependent texture, dietary factors, abnormality spatial location and physical activity.

BRIEF DESCRIPTION OF DRAWINGS

For a fuller understanding of the nature and objects of the invention, reference should be made to the following detailed description, taken in connection with the accompanying drawings, in which:

FIG. 1 shows Equations 1-6;

DETAILED DESCRIPTION

Figure 2:
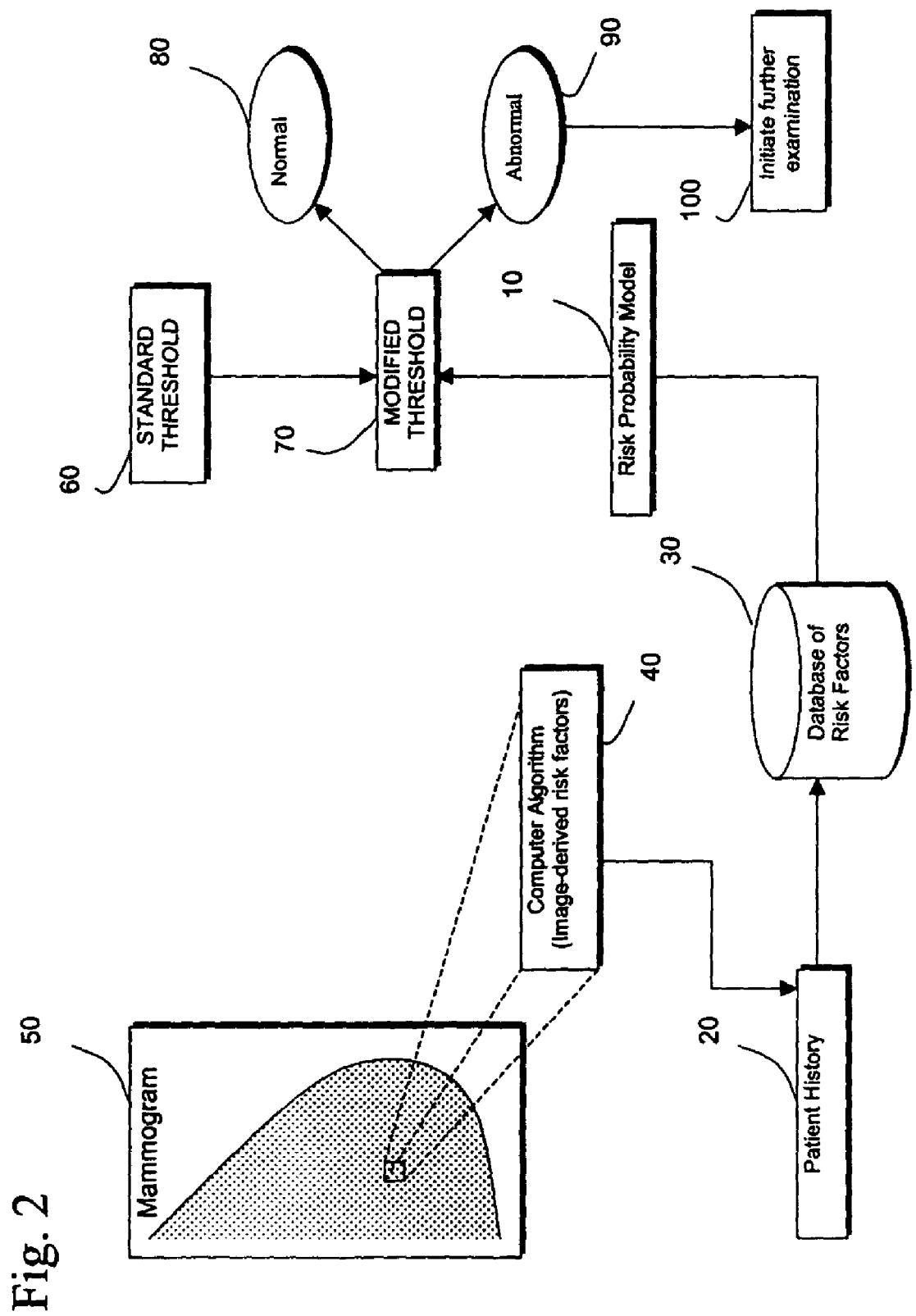
FIG. 2 is a diagrammatic view of the method according to the invention.

There are various ways of modeling risk dependent on the experimental design. The resulting risk figures of merit are often expressed as an odds ratio (OR), relative risk (RR), or absolute risk (AR). In general, RR can be calculated from an incidence study (or often termed cohort study), where a group is tracked over time and the incidence of the disease is monitored. OR can be calculated from a case-control study, which under certain conditions can be used to estimate the RR even though the study design does not strictly support the calculation. The RR estimates from case-control studies often agree with the associated RR calculated from cohort studies of the same population. The AR can be estimated by understanding the RR associated with a given population for a given set of risk factors in addition to understanding the baseline incidence for a patient without any of the risk factors considered.

A brief overview of methods used for estimating risk will be presented here. The three risk estimates described above can be incorporated into CAD analysis. This is in no way a complete discussion of risk analysis, but does provide sufficient background to fuse risk analysis with CAD.

Logistic regression techniques can be applied to case-control studies for estimating for calculating ORs. This is a useful approach when the observed outcome P is dichotomous or restricted to two values representing the occurrence (P=1) or nonoccurrence of some disease (P=1) (P=0) (See FIG. 1, Equation 1). The model is given by FIG. 1, Equation 2 where the x's are the independent variables and the c's are the regression coefficients. Here the independent variables are the risk factors, which can be dichotomous or continuous. For example, mammographic density can be represented as total density or by proportions or by view; similarly weight and height are continuous as well as years of menstruation; family history can be represented dichotomously as 1 if present and 0 if not. Standard methods of forward or backward selection can be applied to determine the significance of a particular risk factor. Or, more generally, conditional logistic regression can be applied to determine the model. All standard risk factors are explored, which include age, density, FH, reproductive years, parous information, weight, height, and other reproductive history, such as age of menarche and age at menopause. It may be the case the two models should be developed depending on menopausal status. This work can be implemented by standard case-control methods. When sampling a database and implementing a case-control study, normally ORs are readily assessable. When certain conditions apply, ORs can be used as an approximation for RR.

There is a different y for each woman (or patient) that makes up the data set. In order to apply this technique, a training data set must be constructed that includes a distribution of women resembling that found in the screening environment. The regression coefficients are found by fitting the model with the risk variables measure from the training set. The training set includes women with the various risk factors with and without the incidence of cancer. Ideally, the cases will be sampled randomly from the two pools (those with and without cancer).

One method of estimating the absolute risk of associated with the disease over some time interval is to use the Gail model approach. Rather than developing the Gail approach specifically, the necessary background from reliability theory is provided, from which the many other approaches follow or are derived from.

In component reliability analysis, the failure rate $\lambda$ (t) plays an important role. There is an analogous expression in survival analysis termed the death rate, which is sometimes referred to as the hazard function. Let f(t) represent the probability density (pdf) for survival time with corresponding cumulative probability F(t). The death rate (or the incidence of some event) is then the rate at which the deaths occur divided by the proportion of the surviving population is provided in FIG. 1, Equation 3 with the obvious substitution. S(t) is referred to as the survivor function (or in reliability theory the probability that component will not fail before time t). In the present invention $\lambda$ (t) is the rate at which the disease occurs (more appropriately the age) or the age-specific incidence rate. The standard solution is provided in FIG. 1, Equation 4. If $\lambda$ (t) is under some form of stress (the analogy here is risk), denoted by x, with pdf p(x), where x in the most general terms is multivariate, we can then express the observed incidence rate in terms of the conditional incidence rate in FIG. 1, Equation 5. The proportional hazard model is written in FIG. 1, Equation 6 for a particular set of risk factors x, where $\lambda_0$ (t) is the baseline hazard when all the covariates are zero, and the β's are the regression parameters. Now Equation 6 can be used to derive the probability of the incidence of the disease over some time period for a patient with a given set of risk parameters.

We have provided for the most part parametric methods for estimating risk. These methods are not exclusive. The embodied ideas of this invention are not restricted to these methods of calculating risk with a given set of risk factors. The ideas discussed here may also be implemented with nonparametric methods.

In FIG. 2, a risk probably value associated with a patient is established 10 from the patient"s history 20 and factors derived from the image, such as density, in view of weighted risk factors 30, the risk probability value calculated from an array of risk factors associated with breast cancer. A computer algorithm 40 adapted to find abnormalities in the patient's mammogram 50 is applied. A standard threshold 60 represents the tolerance level of the algorithm for identifying abnormalities independent of specific patient risk information. The standard tolerance level 60 for false positive results is increased in the computer algorithm 40 responsive to a higher probability value associated with the patient and decreased for false positive results responsive to a lower probability value associated with the patient forming a modified threshold 70 for detection. Under the modified threshold 70, examined tissue is identified as normal 80 or abnormal 90. For results that indicate abnormalities, the mammogram 50 is flagged for further examination 100.

Figure 3:
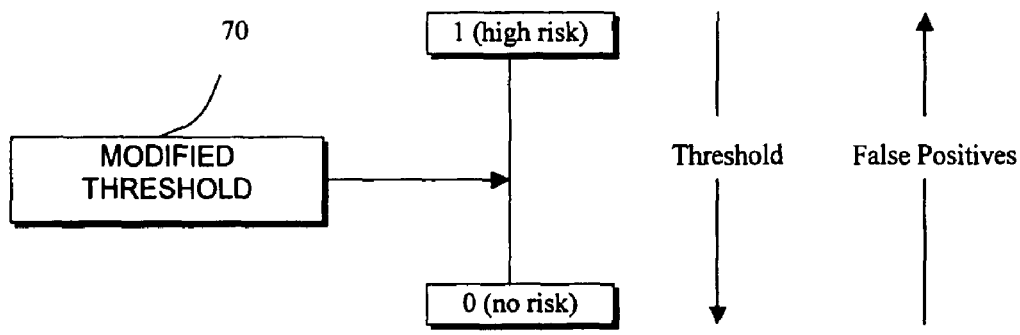
FIG. 3 is a diagrammatic view of detection criteria damped according to risk.

In FIG. 3, the modified threshold 70 is variable from zero to one representing no risk to high risk respectively. By raising the threshold 70, false positives are decreased. Conversely, by lowering the threshold, false positives are increased. As there are finite resources for analyzing mammograms, adjusting the tolerance level for false positives optimizes the limited resources available. Patients at high risk should have a higher tolerance for false positives while patients at low risk should have a relatively lower tolerance for false positives.

The risk factors may include relative risk values, odds ratio values or absolute risk values depending on the screening situation and patient background. An advantage of the present invention is its utility in automated screening. Accordingly, an embodiment of the invention includes the steps of obtaining a patient-specific breast tissue density value derived by automated means from the patient's mammogram and integrating the breast tissue density value in the first in the risk assessment and then into the ensuing detection algorithm(s). Mammograms generating a positive result for breast cancer are flagged for additional analysis. A recommended course of action may be automatically generated wherein more invasive procedures are recommended responsive to the higher probability value and less invasive procedures are recommended responsive to the lower probability value.

In another embodiment, a data entry interface adapted to input the array of risk factors associated with the patient is provided and the patient's mammogram is digitally acquired. The array of risk factors is stored on an electronic storage medium communicatively coupled to the digitally acquired mammogram. The algorithm is applied to the mammogram to find abnormalities. Optionally, mammograms associated with abnormal risk findings are electronically presented with computer aided enhancement.

Figure 4:
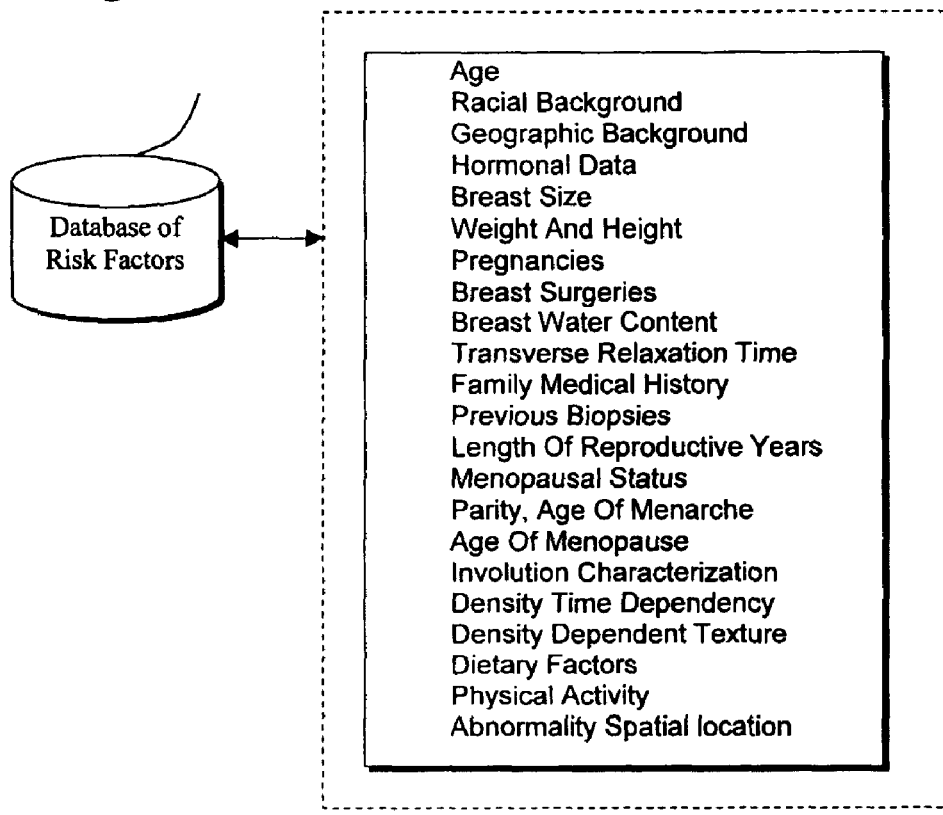
FIG. 4 is a diagrammatic view of a plurality of patient history variables that affect breast cancer risk as integrated into the present invention.

The array of risk factors shown in FIG. 4 includes at least one factor selected from a group of factors including age, racial background, geographic background hormonal data, breast size, weight and height, pregnancies, breast surgeries, breast water content, transverse relaxation time, family medical history, previous biopsies, length of reproductive years, menopausal status, parity, age of menarche, age of menopause, involution characterization, density time dependency, density dependent texture, dietary factors, abnormality spatial location and physical activity. It should be noted that the present invention anticipates numerous factors that affect breast cancel risk and the enumerated variables should not be considered exhaustive.

The risk probability model (either relative or probability of incidence over some specified period) can be used to adjust detection thresholds. The cumulative probability function or relative risk), or integrated probability distribution function of some time interval, has function values (or point value for the latter) ranging from 0 (no risk) to 1 (high risk). As shown in FIG. 3, once acceptable detection sensitivity (high true positive detection rates) is achieved without considering risk, the detection criteria can be damped according to the risk. Note that for high-risk cases the detection sensitivity remains nearly the same (for example, multiply by one), and that for low-risk cases the FP rate will be reduced because the sensitivity rate is reduced (errors move in tandem up and down). Put simply, for high-risk cases the acceptability of FP errors should be increased, and for low-risk cases the FP acceptability should be reduced. This should also support normal image detection algorithm performance increases. Moreover, since the majority of mammographic screening cases are normal, it may be possible to discard a proportion of cases by risk analysis alone. This can be implemented in three distinct ways: (1) with OR considerations, (2) through relative risk analysis, or (3) through estimating the risk over some specified time interval, which leads to an absolute risk figure. All figures of merit have significance, in that the former two may be useful for estimating the relative risk or OR of BC today and the latter for estimating the risk in the serial screening case; all figures of merit may be used in conjunction with the radiologist's assessment as well as with CAD.

REFERENCES IN SUPPORT OF SPECIFICATION

The following citations are incorporated herein by reference:

Adler O B, Engel A. Invasive lobular cacinoma. Mammographic pattern. Rofo Fortschr Geb Rontgenstr Neuen Bildgeb Verfahr 1990; 152:460-462.

Anderson T J, Battersby S, King R J B, McPherson K, Going J J. Oral contraceptive use influences resting breast proliferation. Human Pathology 1989; 20:1139-1144.

Andersson I, Andren L, Pettersson H. Influence of age at first pregnancy on breast parenchymal pattern: A preliminary report. Radiology 1978; 126:675-676.

Andersson I, Janzon L, Pettersson H. Radiographic patterns of the mammary parenchyma: variation with age at examination and age at first birth. Radiology 1981; 138:59-62.

Arthur J E, Ellis I O, Flowers C, Roebuck E, Elston C W, Blamey W. The relationship of "high risk" mammographic patterns to histological risk factors for development of cancer in the human breast. British Journal of Radiology 1990; 63:845-849.

Atkinson C, Warren R, Bingham S A, Day N E. Mammographic patterns as a predictive biomarker of breast cancer risk: effect of tamoxifen. Cancer Epidemiology Biomarkers and Prevention 1999; 8:863-866.

Baasch M, Nielsen S F, Engholm G, Lund K. Breast cancer incidence subsequent to surgical redcution of the female breast. British Journal of Cancer 1996; 73:961-963.

Baines C J, Vidmar M, McKeown-Eyssen G, Tibshirani R. Impact of menstrual phase on false-negative mammograms in the Canadian National Breast Screening Study. Cancer 1997; 80:720-724.

Baines C J. Menstrual cycle variation in mammographic breast density: So who cares? Journal of the National Cancer Institute 1998; 90:875-876.

Bartow S A, Pathak D R, Mettler F A, Key C R, Pike M C. Breast mammographic pattern: a concatenation of confounding and breast cancer risk factors. American Journal of Epidemiology 1995; 142:813-819.

Bartow S A, Pathak D R, Mettler F A. Radiographic microcalcification and parenchymal pattern as indicators of histologic "high-risk" benign breast disease. Cancer 1990; 66:1721-1725.

Beijerinck D, van Hood P A H, Seidell J C, den Tonkelarr I, Rombach J J, Bruning P F. Abdominal fat predominance in women is associated with a decreased prevalence of the high risk P2, DY mammographic breast patterns. International Journal of Obesity 1991; 15:89-93.

Beijerinck D, van Noord P A, Kemmeren J M, Seidell J C. Breast size as a determinant of breast cancer. International Journal of Obesity and Related Metabolic Disorders 1995; 19(3):202-205.

Bergkvist L, Tabar L, Adami H O, Persson I, Bergstrom R. Mammographic parenchymal patterns in women receiving noncontraceptive estrogen treatment. American Journal of Epidemiology 1989; 130:503-510.

Bergkvist L, Tabar L, Bergstrom R, Adami H O. Epidemiologic determinants of the mammographic parenchymal pattern. American Journal of Epidemiology 1987; 126: 1075-1081.

Berkowitz J E, Gatewood O M B, Goldblum L E, Gayler B W. Hormonal replacement therapy: mammographic manifestations. Radiology 1990; 174:199-201.

Bernardes Jr J R M, Nonogaki S, Seixas M T, Rodriques de Lima G, Baracat C, Gebrim L H. Effect of half dose of tamoxifen on proliferative activity in normal breast tissue. International Journal of Gynecology and Obstetrics 1999; 67:33-38.

Bird R E, Wallace T W, Yankaskas B C. Analysis of cancers missed at screening mammography. Radiology 1992; 184: 613-617.

Bland K I, Buchanan J B, Weisberg B F, Hagan T A, Gray L A. The effects of exogenous estrogen replacement therapy of the breast: breast cancer risk and parenchymal patterns. Cancer 1980; 45:3027-3033.

Bland K I, Kuhns J G, Buchanan J B, Dwyer P A, Heuser L F, O'Connor C A et al. A clinicopathologic correlation of mammographic parenchymal patterns and associated risk factors for human mammary carcinoma. Annals of Surgery 1982; 195:582-594.

Boice J D Jr, Friis S, McLaughlin J K, Mellemkjaer L, Blot W J, Fraumeni J F Jr et al. Cancer following breast reduction surgery in Denmark. Cancer Causes and Control 1997; 8:253-258.

Boice J D Jr, Persson I, Brinton L A, Hober M, McLaughlin J. K., Blot W J et al. Breast Cancer following Breast Reduction Surgery in Sweden. Plastic And Reconstructive Surgery 2000; 106:755-762.

Boyd N, Lockwood G A, Martin L J, Byng J W, Yaffe M, Tritchler D L. Mammographic density as a marker of susceptibility to breast cancer: a hypothesis. Biomarkers in Cancer Chemoprevention 2001; 154:163-169.

Boyd N, O'Sullivan B, Campbell J E, Fishell E, Simor I, Cooke G et al. Bias and the Asscociation of Mammographic Parenchymal Patterns With Breast Cancer. British Journal of Cancer 1982; 45:179-184.

Boyd N F, Byng J W, Jong R A, Fishell E K, Little L E, Miller A B et al. Quantitative classification of mammographic densities and breast cancer risk:results from the Canadian National Breast Screening Study. Journal of the National Cancer Institute 1995; 87:670-675.

Boyd N F, Cousins M, Beaton M, Fishell E, Wright B, Fish E et al. Clinical trial of low-fat, high-carbohydrate diet in subjects with mammographic dysplasia: report of early outcomes. Journal of the National Cancer Institute 1988; 80:1244-1248.

Boyd N F, Greenberg C, Lockwood G, Little L, Martin L J, Byng J W et al. Effects at two years of a low-fat, high-carbohydrate diet on radiologic features of the breast: results from a randomized trial. Journal of the National Cancer Institute 1997; 89:488-496.

Boyd N F, Jensen H M, Cooke G, Han H L. Relationship between mammographic and histological risk factors for breast cancer. Journal of the National Cancer Institute 1992; 84:1170-1179.

Boyd N F, Lockwood G A, Byng J W, Little L E, Yaffe M J, Tritchler D L. The relationship of anthropometric measures to radiological features of the breast in premenopausal women. British Journal of Cancer 1998; 78:1233-1238.

Boyd N F, Lockwood G A, Byng J W, Tritchler D L, Yaffe M J. Mammographic densities and breast cancer risk. Cancer Epidemiology Biomarkers and Prevention 1998; 7:1133-1144.

Boyd N F, Lockwood G A, Martin L J, Knight J A, Jong R A, Fishell E et al. Mammographic densities and risk of breast cancer among subjects with a family history of this disease. Journal of the National Cancer Institute 1999; 91:1404-1408.

Boyd N F, McGuire V, Fishell E, Kuriov V, Lockwood G, Tritchler D L. Plasma lipids in premenopausal women with mammographic dysplasia. British Journal of Cancer 1989; 59:766-771.

Boyd N F, McGuire V. Evidence of association between plasma high-density lipoprotein cholesterol and risk factors for breast cancer. Journal of the National Cancer Institute 1990; 82:460-468.

Boyd N F, O'Sullivan B, Campbell J E, Fishell E, Simor I, Cooke G et al. Mammographic signs as risk factors for breast cancer. British Journal of Cancer 1982; 45:185-193.

Boyd N F, O'Sullivan B, Fishell E, Simor I, Cooke G. Mammographic patterns and breast cancer risk: methodologic standards and contradictictory results. Journal of the National Cancer Institute 1984; 72:1253-1259.

Brebner D M, Epstein E E, Lange M. Xerographic parenchymal patterns and breast cancer. South African Medical Journal 1978; 54:853-856.

Brekelmans C T M, Collette H J, Collette C, Frachebound J, de Waard F. Breast cancer after a negative screen: follow-up of women participating in the DOM screening programme. European Journal of Cancer 1992; 28A(4-5):893-895.

Brekelmans C T M, Westers P, Faber J A J, Peeters P H M, Collette H J A. Age specific sensitivity and sojourn time in a breast cancer screening programme (DOM) in The Netherlands: a comparison of different methods. Journal of Epidemiology and Community Health 1996; 50:68-71.

Breuer B, Miller D G, Salane M, Wolfe J N. Mammographic parenchymal patterns and family history of breast cancer. Cancer 1992; 69:602.

Brinton L A, Persson I, Boice J D Jr, McLaughlin J. K., Fraumeni J F Jr. Breast Cancer Risk in Relation to Amount of Tissue Removed during Breast Reduction Operations in Sweden. Cancer 2001; 91:478-483.

Brisson J, Brisson B, Cote G, Maunsell E, Berube S, Robert J. Tamoxifen and Mammographic Breast Densities. Cancer Epidemiology Biomarkers and Prevention 2000; 9:911-915.

Brisson J, Merletti F, Sadowsky N L, Twaddle J A, Morrison A S, Cole P. Mammographic features of the breast and breast cancer risk. American Journal of Epidemiology 1982; 115:428-437.

Brisson J, Morrison A S, Khalid N. Mammographic pernchymal features and breast cancer in the breast cancer detection demonstration project. Journal of the National Cancer Institute 1988; 80:1534-1540.

Brisson J, Morrison A S, Kopans D B, Sadowsky N L, Kalisher L, Twaddle J A et al. Height and weight, mammographic features of breast tissue, and breast cancer risk. American Journal of Epidemiology 1984; 119:371-381.

Brisson J, Sadowsky N L, Twaddle J A, Morrison A S, Cole P, Merletti F. The relation of mammographic features of the breast to breast cancer risk factors. American Journal of Epidemiology 1982; 115:438-443.

Brisson J, Verreault R, Morrison A S, Tennina S, Meyer F. Diet, mammographic features of breast tissue, and breast cancer risk. American Journal of Epidemiology 1989; 130: 14-24.

Brisson J. Family history of breast cancer, mammographic features of breast tissue, and breast cancer risk. Epidemiology 1991; 2:440-444.

Bucchi L, Costantini M, Buzzi G, Bravetti P, Cicognani A, Torta M et al. Wolfe's mammographic patterns in women with gross cystic disease of the breast. Journal of Clinical Epidemiology 1995; 48:969-976.

Buchanan J B, Spratt J S, Heuser L S. Tumor growth, doubling times, and the inability of the radiologist to diagnose certain cancers. Radiologic Clinics of North America 1983; 21:115-126.

Buchanan J B, Weisberg B F, Sandoz J P, Gray Sr. L A, Bland K I. Selected prognastic variables for mammographic parenchymal variables. Cancer 1981; 47:2135-2137.

Burhenne H J, Burhenne L W, Goldberg F, Hislop T G, Worth A J, Rebbeck P M et al. Interval breast cancers in the screening mammography program of British Columbia: analysis and classification. American Journal of Roentgenology 1994; 162:1067-1071.

Burrell H C, Sibbering D M, Wilson A R M, Pinder S E, Evans A J, Yeoman L J et al. Screening interval breast cancers: mammographic features and prognastic factors. Radiology 1996; 199:811-817.

Byng J W, Boyd N F, Fishell E, Jong R A, Yaffe M J. The quantitative analysis of mammographic densities. Physics in Medicine and Biology 1994; 39:1629-1638.

Byng J W, Boyd N F, Little L, Lockwood G, Fishell E, Jong R A et al. Symmetry of projection in the quantitative analysis of mammographic images. European Journal of Cancer Prevention 1996; 5:319-327.

Byng J W, Yaffe M, Jong R A, Shumak R S, Lockwood G A, Math M et al. Analysis of Mammographic Density and Breast Cancer Risk from Digitized Mammograms. RadioGraphics 1998; 18:1587-1598.

Byng J W, Yaffe M J, Lockwood G A, Little L E, Tritchler D L, Boyd N F. Automated analysis of mammographic densities and breast carcinoma risk. Cancer 1997; 80:66-74.

Byrne C, Schairer C, Wolfe J, Parekh N, Salane M, Brinton L A et al. Mammographic features and breast cancer risk: effects with time, age, and menopause status. Journal of the National Cancer Institute 1995; 87:1622-1629.

Byrne C. Studying mammographic density: implications for understanding breast cancer. Journal of the National Cancer Institute 1997; 89:531-533.

Caldwell C B, Stapleton S J, Holdsworth D W, Jong R A, Weiser W J, Cooke G et al. Characterisation of mammographic parenchymal pattern by fractal dimension. Physics in Medicine and Biology 1990; 35:235-247.

Carlile T, Kopecky K J, Thompson D J, Whitehead J R, Gilbert Jr F I, Present A J et al. Breast cancer prediction and the Wolfe classification of mammograms. Journal of the American Medical Association 1985; 254:1050-1053.

Chaudary M A, Gravelle I H, Bulstrode J C, Wang D Y, Bulbrook R D, Millis R R et al. Breast parenchymal patterns in women with bilateral primary breast cancer. The British Journal of Radiology 1983; 56:703-706.

Chow C K, Venzon D, Jones E C, Premkumar A, O'Shaughnessy J, Zujewski J. Effect of tamoxifen on mammographic density. Cancer Epidemiology Biomarkers and Prevention 2000; 9:917-921.

Ciatto S, Bravetti P, Cecchini S, Cirillo A. Mammographic parenchymal patterns and breast cancer risk. La Radiologia Medica 1990; 79:346-348.

Ciatto S, Rosselli del Turco M, Zappa M. The detectability of breast cancer by screening mammography. British Journal of Cancer 1995; 71:337-339.

Ciatto S, Zappa M. A prospective study of the value of mammographic patterns as indicators of breast cancer risk in a screening experience. European Journal of Radiology 1993; 17:122-125.

Cowan D F, Herbert T A. Involution of the breast in women aged 50 to 104 years: a histopathological study of 102 cases. Surgical Pathology 1989; 2:323-333. Cowan W K, Angus B, Gray J C, Lunt L G, Ramedan A l-Tamimi S. A study of interval breast cancer within the NHS breast screening programme. Journal of Clinical Pathology 2000; 53:140-146.

Cyrlak D, Wong H. Mammographic changes in postmenopausal women undergoing hormonal replacement therapy. American Journal of Roentgenol 1993; 161:1177-1183.

Daly C A, Apthorp L, Field S. Second round cancers: how many were visible on the first round of the U K National Breast Cancer Screening Programme, three years earlier? Clinical Radiology 1998; 53:25-28.

Day N E, Walter S D. Simplified models of screening for chronic disease: estimation procedures from mass screening programs. Biometrics 1984; 40:1-14.

de Rijke J M, Schouten L J, Schreutelkamp J L, Jochem I, Verbeek A L. A blind review and an informed review of interval breast cancer rates in the Limburg screening programme, the Netherlands. Journal of Medical Screening 2000; 7(1):19-23.

De Stavola B L, Gravelle I H, Wang D Y, Allen D S, Bulbrook R D, Fentiman I S et al. Relationship of mammographic parenchymal patterns with breast cancer risk factors and risk of breast cancer in a prospective study. International Journal of Epidemiology 1990; 19:247-254.

de Waard F, Rombach J J, Collette H J A, Slotboom B. Breast cancer risk associated with reproductive factors and breast parenchymal patterns. Journal of the National Cancer Institute 1984; 72:1277-1282.

DeGroote R, Rush B F, Milazzo J, Warden M J, Rocko J M. Interval breast cancer: A more aggressive subset of breast neoplasias. Surgery 1983; 94:543-547.

Doyle G J, McLean L. Unilateral increase in mammographic density with hormone replacement therapy. Clinical Radiology 1994; 49:50-51.

Doyle P J, Blarney R W, Chaffe A, Roebuck E. Rate of breast cancer related to parenchymal pattern of mammogram. Clinical Oncology 1979; 5:390-391.

Duffy S W, Chen H H, Tabár L, Day N E. Estimation of mean sojourn time in breast cancer screening using a Markov chain model of both entry to and exit from preclinical detectable phase. Statistics in Medicine 1995; 14:1531-1543.

Duffy S W, Chen H H, Tabár L, Fagerberg G, Paci E. Sojourn time, sensitivity, and positive predictive value of mammography screening for breast cancer in women aged 40-49. International Journal of Epidemiology 1996; 25:1139-1145.

Duffy S W, Day N E, Tabár L, Chen H H, Smith T C. Markov models of breast tumor progression: some age-specific results. Journal of the National Cancer Institute Monographs 1997; 22:93-97.

Egan R L, McSweeney M B. Mammographic parenchymal patterns and risk of breast cancer. Radiology 1979; 133: 65-70.

Egan R L, Mosteller R C. Breast cancer mammography patterns. Cancer 1977; 40:2087-2090.

Ekbom A, Thurfjell E, Hsieh C C, Trichopoulos D, Adami H O. Perinatal characteristics and adult mammographic patterns. International Journal of Cancer 1995; 61:177-180.

El-Bastawissi A Y, White E, Mandelson M T, Taplin S. Variation in Mammographic Breast Density by Race. Annals of Epidemiology 2001; 11:257-263.

Ernster V L, Sacks S T, Peterson C A, Schweitzer R J. Mammographic parenchymal patterns and risk factors for breast cancer. Radiology 1980; 134:617-620.

Farewell V T, Math B, Math M. The combined effect of breast cancer risk factors. Cancer 1977; 40:931-936.

Feig S A. Hormonal reduction of mammographic densities: potential effects on breast cancer risk and diagnostic and screening mammography. Journal of the National Cancer Institute 1994; 86:408-409.

Fewins H E, Whitehouse G H, Leinster S J. Changes in breast parenchymal patterns with increasing age. Breast Diseases 1990; 3:145-151.

Fioretti F, Tavani A, Bosetti C, La Vecchia C, Negri E, Barbone F et al. Risk factors for breast cancer in nulliparous women. British Journal of Cancer 1999; 79:1923-1928.

Fisher E R, Palekar A, Kim W S, Redmond C. The histopathology of mammographic patterns. American Journal of Clinical Pathology 1978; 69:421-426.

Fletcher S W, Black W, Harris R, Rimer B K, Shapiro S. Report on the International Workshop on Screening for Breast Cancer. Journal of the National Cancer Institute 1993; 85:1644-1656.

Flook D, Gilhome R W, Harman J, Gravelle I H, Webster D J T. Changes in Wolfe mammographic patterns with aging. The British Journal of Radiology 1987; 60:455-456.

Fowler P A, Casey C E, Cameron G G, Foster M A, Knight C H. Cyclic changes in composition and volume of the breast during the menstrual cycle, measured by magnetic resonance imaging. British journal of Obstetrics and Gynecology 1990; 97:595-602.

Foxcroft L M, Evans E B, Joshua H K, Hirst C. Breast cancers invisible on mammography. Australian and New Zealand Journal of Surgery 2000; 70:162-167.

Freedman M, San Martin J, O'Gorman J, Eckert S, Lippman M E, Lo S-C B et al. Digitized Mammography: a Clinical Trial of Postmenopausal Women Randomly Assigned to Receive Raloxifene, Estrogen, or Placebo. Journal of the National Cancer Institute 2001; 93(1):51-56.

Friedenreich C M, Thune I, Brinton L A, Albanes D. Epidemiologic issues related to the association between physical activity and breast cancer. Cancer 1998; 83:600-610.

Funkhouser E, Waterbor J W, Cole P, Rubin E. Mammographic patterns and breast cancer risk factors among women having elective screening. Southern Medical Journal 1993; 86:177-180.

Gail M H, Brinton L A, Byar D P, Corle D K, Green S B, Schairer C et al. Projecting individualized probablities of developing breast cancer for white females who are being examined annually. Journal of the National Cancer Institute 1989; 81:1879-1886.

Gajdos C, Tartter P I, Bleiweiss I J, Bodian C, Brower S T. Stage 0 to stage III breast cancer in young women. Journal of the American College of Surgeons 2000; 190:509-515.

Gertig D M, Stillman I E, Byrne C, Spiegelman D, Schnitt S J, Connolly J L et al. Association of age and reproductive factors with benign breast tissue composition. Cancer Epidemiology Biomarkers and Prevention 1999; 8:873-879.

Gilliland F D, Joste N. Stauber P M, Hunt W C, Rosenberg R, Redlich G et al. Biologic characteristics of interval and screen-detected breast cancers. Journal of the National Cancer Institute 2000; 92:743-748.

Goergen S K, Evans J, Cohen G P B, MacMillan J H. Characteristics of breast carcinomas missed by screening radiologists. Radiology 1997; 204:131-135.

Going J J, Anderson T J, Battersby S, MacIntyre C C A. Proliferative and secretory activity in human breast during natural and artificial menstrual cycles. American Journal of Pathology 1988; 130:193-204.

Goodwin J J, Boyd N F. Mammographic parenchymal pattern and breast cancer risk: a critical appraisal of the evidence. American Journal of Epidemiology 1988; 127:1097-1108.

Graham S J, Bronskill M J, Byng J W, Yaffe M, Boyd N F. Quantitative correlation of breast tissue parameters using magnetic resonance and X-ray mammography. British Journal of Cancer 1996; 73:162-168.

Graham S J, Stanchev P L, Lloyd-Smith J O A, Bronskill M J, Plewes D B. Changes in fibroglandular volume and water content of breast tissue during the menstrual cycle observed by M R imaging at 1.5 T. Journal of Magnetic Resonance Imaging 1995; 5:695-701.

Gram I T, Funkhouser E, Tabar L. Anthropometric indices in relation to mammographic patterns among peri-menopausal women. International Journal of Cancer 1997; 73:323-326.

Gram I T, Funkhouser E, Tabar L. Moderate physical activity in relation to mammographic patterns. Cancer Epidemiology Biomarkers and Prevention 1999; 8:117-122.

Gram I T, Funkhouser E, Tabar L. Reproductive and menstrual factors in relation to mammographic parenchymal patterns among perimenopausal women. British Journal of Cancer 1995; 71:647-650.

Gravelle I H, Bulstrode J C, Bulbrook R D, Hayward J L, Wang D Y. The relation between radiological patterns of the breast and body weight and height. British Journal of Radiology 1982; 55:23-25.

Gravelle I H, Bulstrode J C, Bulbrook R D, Wang D Y, Allen D S, Hayward J L. A prospective study of mammographic parenchymal patterns and risk of breast cancer. The British Journal of Radiology 1986; 59:487-491.

Gravelle I H, Bulstrode J C, Wang D Y, Hayward J L. The relation between radiographic features and determinants of risk of breast cancer. British Journal of Radiology 1980; 53:107-113.

Greendale G A, Reboussin B A, Sie A, Singh R, Olson L K, Gatewood O et al. Effects of estrogen and estrogen-progestin on mammographic parenchymal density. Annals of Internal Medicine 1999; 130:262-269.

Grove J S, Goodman M J, Gilbert F, Clyde D. Factors associated with breast structure in breast cancer patients. Cancer 1979; 43:1895-1899.

Grove J S, Goodman M J, Gilbert Jr F I, Mi M P. Factors associated with mammographic pattern. The British journal of Radiology 1985; 58:21-25.

Hainline S, Myers L, McLelland R, Newell J, Grufferman S, Shingleton W./Mammographic patterns and risk of breast cancer. American Journal of Roentgenology 1978; 130: 1157-1158.

Hakama M, Holli K, Isola J, Kallioniemi O P, Kärkkäinen A, Visakorpi T et al. Aggressiveness of screen-detected breast cancers. The Lancet 1995; 345:221-223.

Hart B L, Steinbock R T, Mettler Jr F A, Pathak D R, Bartow S A. Age and race related changes in mammographic parenchymal patterns. Cancer 1989; 63:2537-2539.

Heimann R, Bradley J, Hellman S. The benefits of mammography are not limited to women of ages older than 50 years. Cancer 1998; 82:2221-2226.

Heine J J, Deans S R, Clarke L P. Multiresolution Probability Analysis of Random Fields. Journal of the Optical Society of America A 1999; 16:6-16.

Heine J J, Deans S R, Cullers D K, Stauduhar R, Clarke L P. Multiresolution probability analysis of gray scaled images. Journal of the Optical Society of America A 15, 1048-1058.1998.

Heine J J, Deans S R, Cullers D K, Stauduhar R, Clarke L P. Multiresolution statistical analysis of high resolution digital mammograms. IEEE Transactions on Medical Imaging 1997; 16:503-515.

Heine J J, Deans S R, Cullers D K, Stauduhar R, Clarke L P. Multiresolution probability analysis of gray scaled images. Journal of the Optical Society of America A 15, 1048-1058.1998. Ref Type: GenericHeine J J, Deans S R, Gangadharan D, Clarke L P. Multiresolution Analysis of Two Dimensional 1/f Processes: Approximations for random variable transformations. Optical Engineering 1999; 38:1505-1516.

Heine J J, Deans S R, Velthuizen R P, Clarke L P. On the Statistical Nature of Mammograms. Medical Physics 1999; 26:2254-2265.

Heine J J, Velthuizen R P. A statistical methodology for mammographic density detection. Medical Physics 2000; 27(12):2644-2651.

Heine J J, Velthuizen R P. Spectral Analysis of FFDM Data. Medical Physics 2001.

Henson D E, Tarone R E. Involution and the etiology of breast cancer. Cancer 1994; 74:424-429.

Henson D E, Tarone R E. On the possible role of involution in the natural history of breast cancer. Cancer 1993; 71:2154-2156.

Herrinton L J, Saftlas A F, Stanford J L, Brinton L A, Wolfe J N. Do alcohol intake and mammographic densities interact in regard to the risk of breast cancer? Cancer 1993; 71:3029-3035.

Heuser L S, Spratt J S, Kuhns J G, Chang AFC, Polk H C, Buchanan J B. The association of pathologic and mammographic characteristics of primary human breast cancers with "slow" and "fast" growth rates and with axillary lymph node metastases. Cancer 1984; 53:96-98.

Hoffman-Goetz L, Apter D, Denmark-Wahnefried W, Goran M I, McTiernan A, Reichman M E. Possible mechanisms mediating association between physical activity and breast cancer. Cancer 1998; 83:621-628.

Hofseth L J, Raafat A M, Osuch J R, Pathak D R, Slomski C A, Haslam S Z. Hormone replacement therapy with estrogen or estrogen plus medroxprogesterone acetate is associated with increased epithelial proliferation in the normal postmenopausal breast. Journal of Clinical Endocrinology and Metabolism 1999; 84:4559-4565.

Holland R, Hendriks JHCL, Mravunac M. Mammography occult breast cancer. A pathologic and radiologic study. Cancer 1983; 52:1810-1819.

Holmberg L, Baron J A, Byers T, Wolk A, Ohlander E M, Zack M et al. Alcohol intake and breast cancer risk: effect of exposure from 15 years of age. Cancer Epidemiology Biomarkers and Prevention 1995; 4:843-847.

Horwitz R I, Lamas A M, Peck D. Mammographic parenchymal patterns and risk of breast cancer in postmenopausal women. The American Journal of Medicine 1984; 77:621-624.

Hrushesky W J. Mammography and the menstrual cycle. International Journal of Cancer 1994; 59:151.

Hsieh C, Pavia M, Lambe M, Lan S J, Colditz G A, Ekbom A et al. Dual effect of parity on breast cancer risk. European Journal of Cancer 1994; 30A:969-973.

Huo Z, Giger M L, Wolverton D E, Zhong, Cumming S, Olopade O I. Computerized analysis of mammographic parenchymal patterns for breast cancer risk assessment: Feature selection. Medical Physics 2000; 27(1):4-12.

Hutson S W, Cowen P N, Bird C C. Morphometric studies of age related changes in normal human breast and their significance for evolution of mammary cancer. Journal of Clinical Pathology 1985; 38:281-287.

Jacobs H S. Hormone replacement therapy and breast cancer. Endocrine-Related Cancer 2000; 7:53-61.

Jakes R W, Duffy S W, Ng F C, Gao F, Ng E H. Mammographic parenchymal patterns and risk of breast cancer at and after a prevalence screen in Singaporean women. International Journal of Epidemiology 2000; 29:11-19.

Janzon L, Andersson I, Petersson H. Mammographic patterns as indicators of risk of breast cancer. A cross-sectional population study. Diagnostic Radiology 1982; 143:417-419.

Jenks S. Dense breast tissues may hold increased cancer risk for some. Journal of the National Cancer Institute 1994; 86:578-580.

Kaaks R, van Noord P A H, Tonkelaar I D, Peeters P H M, Riboli E, Grobbee D E. Breast-Cancer Incidence in Relation to Height, Weight and Body-Fat Distribution in the Dutch "DOM" Cohort. International Journal of Cancer 1998; 76:647-651.

Kallergi M, Woods K, Clarke L P, Qian W, Clark R A. Image segmentation in digital mammography: comparison of local thresholding and region growing algorithms. Computerized Medical Imaging and Graphics 1992; 16:323-331.

Kampert J B, Whittemore A S, Paffenbarger Jr. R S. Combined effect of childbearing, menstrual events, and body size on age-specific breast cancer risk. American Journal of Epidemiology 1988; 128:962-979.

Kaprio J, Alanko A, Kivisaari L, Standertskjöld-Nordenstam C G. Mammographic patterns in twin pairs discordant for breast cancer. The British Journal of Radiology 1987; 60:459-462.

Karssemeijer N. Automated classification of parenchymal patterns in mammograms. Physics in Medicine and Biology 1998; 43:365-378.

Kato I, Beinart C, Bleich A, Su S, Kim M, Toniolo P G. A nested case-control study of mammographic patterns, breast volume, and breast cancer (New York City, N.Y., United States). Cancer Causes and Control 1995; 6:431-438.

Kaufman Z, Garstin W I H, Hayes R, Michell M J, Baum M. The mammographic parenchymal patterns of women on hormonal replacement therapy. Clinical Radiology 1991; 43:385-392.

Kaur J S. Migration Patterns and Breast Carcinoma. Cancer Supplement 2000; 88 (5):1203-1206.

Kavanagh A M, Mitchell H, Giles G G. Hormone Replacement therapy and accuracy of mammographic screening. Lancet 2000; 355:270-274.

Kerlikowske K, Grady D, Barclay J, Sickles E A, Ernster V. Effect of age, breast density, and family history on the sensitivity of first screening mammography. Journal of the American Medical Association 1996; 276:33-38.

Kerlikowske K, Grady D, Barclay J, Sickles E A, Ernster V. Likelihood ratios for modern screening mammography: risk of breast cancer based on age and mammographic interpretation. Journal of the American Medical Association 1996; 276:39-43.

Klemi P J, Toikkanen S, R ä s ä nen O, Parvinen I, Joensuu H. Mammography screening interval and the frequency of interval cancers in a population-based screening. British Journal of Cancer 1997; 75:762-766.

Knight J A, Martin L J, Greenberg C V, Lockwood G A, Byng J W, Yaffe M J et al. Macronutrient intake and change in mammographic density at menopause: results from a randomized trial. Cancer Epidemiology Biomarkers and Prevention 1999; 8:123-128.

Kostelec P J, Weaver J B, Healy D M Jr. Multiresolution elastic image registration. Medical Physics 1998; 25(9): 1593-1604.

Krook P M, Carlile T, Bush W, Hall M H. Mammographic parenchymal patterns as a risk indicator for prevalent and incident cancer. Cancer 1978; 41:1093-1097.

Krook P M. Mammographic pernchymal patterns as risk indicators for incident cancer in a screening program: an extended analysis. American Journal of Roentgenology 1978; 131:1031-1035.

Kuroishi T, Tominaga S, Morimoto T, Tashiro H, Itoh S, Watanabe H et al. Tumor growth rate and prognosis of breast cancer mainly detected by mass screening. Japanese Journal of Cancer Research 1990; 81:454-462.

Lam P B, Vacek P M, Geller B M, Muss H B. The association of increased weight, body mass index, and tissue density with the risk of breast carcinoma in Vermont. Cancer 2000; 89:369-375.

Laya M B, Gallagher J C, Schreiman J S, Larson E B, Watson P, Weinstein L. Effect of postmenopausal hormonal replacement therapy on mammographic density and parenchymal pattern. Radiology 1995; 196:433-437.

Laya M B, Larson E B, Taplin S H, White E. Effect of estrogen replacement therapy on the specificity and sensitivity of screening mammography. Journal of the National Cancer Institute 1996; 88:643-649.

Lee N A, Rusinek H, Weinreb J, Chandra R, Toth H, Singer C et al. Fatty and fibroglandular tissue volumes in the breasts of women 20-83 years old: comparison of X-ray mammography and computer-assisted M R imaging. American Journal of Roentgenology 1997; 168:501-506.

Lee-Han H, Cooke G, Boyd N F. Quantitaive evaluation of mammographic densities: a comparison of methods of assessment. European Journal of Cancer Prevention 1995; 4:285-292.

Lehman C D, White E, Peacock S, Drucker M J, Urban N. Effect of age and breast density on screening mammograms with false-positive findings. American Journal of Roentgenology 1999; 173:1651-1655.

Leinster S J, Walsh P V, Whitehouse G H, Al-Sumidaie A M. Factors associated with mammographic parenchymal patterns. Clinical Radiology 1988; 39:252-256.

Leinster S J, Whitehouse G H. The mammographic breast pattern and oral contraception. The British Journal of Radiology 1986; 59:237-239.

Leung W, Goldberg F, Zee B, Sterns E. Mammographic density in women on postmenopausal hormone replacement therapy. Surgery 1997; 122:669-674.

Lewin J. M. Full-Field Digital Mammography A Candid Assessment. Diagnostic Imaging, 40-45. 1999. Ref Type: Magazine ArticleLewin J M, Hendrick R A, D'Orsi C J, Isaacs P K, Moss L J, Karelass A et al. Comparison of Full-Field Digital Mammography with Screen-Film Mammography for Cancer Detection: Results of 4,954 Paired Examinations. Radiology 2001; 218(3):873-880.

Lillestrand R L. Techniques for change detection. IEEE Transactions on Computers 1972; c-21:654-659.

Litherland J C, Stallard S, Hole D, Cordiner C. The effect of hormone replacement therapy on the sensitivity of screening mammograms. Clinical Radiology 1999; 54:285-288.

Longnecker M P, Bernstein L, Paganini-Hill A, Enger S M, Ross R K. Risk factors for in situ breast cancer. Cancer Epidemiology Biomarkers and Prevention 1996; 5:961-965.

Lundstr ö m E, Wilczek B, von Palffy Z, S ö derqvist G, von Schoultz B. Mammographic breast density during hormone replacement therapy: differences according to treatment. American Journal of Obstetrics and Gynecology 1999; 181:348-352.

Ma L, Fishell E, Wright B, Hanna W, Allan S, Boyd N F. Case-control study factors associated with failure to detect breast cancer by mammography. Journal of the National Cancer Institute 1992; 84:781-785.

Madigan M P, Ziegler R G, Benichou J, Byrne C, Hoover R N. Proportion of breast cancer cases in the United States explained by well-established risk factors. Journal of the National Cancer Institute 1995; 87:1681-1685.

Magnin I E, Cluzeau F, Odet C L, Bremond A. Mammographic texture analysis: an evaluation of risk for developing breast cancer. Optical Engineering 1986; 25:780-784.

Mandelson M T, Oestreicher N, Porter P L, White D, Finder C L, Taplin S H et al. Breast Density as a Predictor of Mammographic Detection: Comparison of Interval- and Screen-Detected Cancers. Journal of the National Cancer Institute 2000; 92:1081-1087.

Maskarinec G, Lyu L-C, Meng L, Theriault A, Ursin G. Determinants of Mammographic Densities Among Women of Asian, Native Hawaiian, and Caucasian Ancestry. Ethnicity & Disease 2001; 11:44-55.

Maskarinec G, Meng L, Shimozuma K. A pilot study of mammographic density patterns among Japanese women. J Epidemiol 1999; 9:73-77.

McNicholas M M J, Heneghan J P, Milner M H, Tunney T, Hourihane J B, MacErlaine D P. Pain and increased mammographic density in women receiving hormone replacement therapy: a prospective study. American Journal of Roentgenology 1994; 163:311-315.

McSweeney M B. Breast parenchymal patterns as an indicator of risk for developing breast cancer. Journal of the Medical Association of Georgia 1978; 67:413-414.

Mendell L, Rosenbloom M, Naimark A. Are breast patterns a risk index for breast cancer? A reappraisal. American Journal of Roentgenology 1977; 128:547.

Meyer F, Brisson J, Morrison A S, Brown J B. Endogenous sex hormones, prolactin, and mammographic features of breast tissue in premenopausal women. Journal of the National Cancer Institute 1986; 77:617-620.

Moberg K, Grundström H, Törnberg S, Lundquist H, Svane G, Havervall L et al. Two models for radiological reviewing of interval cancers. Journal of Medical Screening 1999; 6:35-39.

Moskowitz M, Gartside P, McLaughlin C. Mammographic patterns as markers for high-risk benign breast disease and incident cancers. Radiology 1980; 134:293-295.

Moskowitz M. Breast cancer: age-specific growth rates and screening strategies. Radiology 1986; 161:37-41.

Muller S. Full-field digital mammography designed as a complete system. European Journal of Radiology 1999; 31(1): 25-34.

Nordevang E, Azavedo E, Svane G, Nilsson R, Holm L E. Dietary habits and mammographic patterns in patients with breast cancer. Breast Cancer Research and Treatment 1993; 26:207-215.

Oza A M, Boyd N F. Mammographic parenchymal patterns: a marker of breast cancer risk. Epidemiologic Reviews 1993; 15:196-208.

Özdemir A, Konus Ö, Nas T, Erbas G, Cosar S, Isik S. Mammographic and ultrasonographic study of changes in the breast related to HRT. International Journal of Gynecology and Obstetrics 1999; 67:23-32.

Paci E, Duffy S W. Modelling the analysis of breast cancer screening programmes: sensitivity, lead time and predictive value in the Florence District Programme (1975-1986). International Journal of Epidemiology 1991; 20:852-858.

Pankow J S, Vachon C M, Kuni C C, King R A, Arnett D K, Grabrick D M et al. Genetic analysis of mammographic breast density in adult women: evidence of a gene effect. Journal of the National Cancer Institute 1997; 89:549-556.

Peer P G M, van Dijck J A A M, Hendriks J H C L, Holland R, Verbeek A L M. Age-dependent growth rate of primary breast cancer. Cancer 1993; 71:3547-3551.

Peeters P H M, Verbeek A L M, Hendriks J H C L, Holland R, Mravunac M, Vooijs G P. The occurence of interval cancers in the Nijmegen screening programme. British Journal of Cancer 1989; 59:929-932.

Persson I, Thurfjell E, Holmberg L. Effect of estrogen and estrogen-progestin replacement regimens on mammographic breast parenchymal density. Journal of Clinical Oncology 1997; 15:3201-3207.

Peyster R G, Kalisher L, Cole P. Mammographic parenchymal patterns and the prevalence of breast cancer. Radiology 1977; 125:387-391.

Piccoli C W, Feig S A, Palazzo J P. Developing asymmetric breast tissue. Radiology 1999; 211:111-117.

Pike M C, Krailo M D, Henderson B E, Casagrande J T, Hoel D G. 'Hormonal' risk factors, 'breast tissue age' and the age-incidence of breast cancer. Nature 1983; 303:767-770.

Pike M C, Spicer D V, Dahmoush L, Press M F. Estrogens, progesterones, normal breast cell proliferation, and breast cancer risk. Epidemiologic Reviews 1993; 15:17-35.

Poon C S, Bronskill M J, Henkelman R M, Boyd N F. Quantitative magnetic resonance imaging parameters and their relationship to mammographic pattern. Journal of the National Cancer Institute 1992; 84:777-781.

Porter P L, El-Bastawissi A Y, Mandelson M T, Lin M G, Khalid N, Watney E A et al. Breast tumor characteristics as predictors of mammographic detection: comparison of interval- and screen-detected cancers. Journal of the National Cancer Institute 1999; 1999:2020-2028.

Powell K A, Obuchowski N A, Davros W J, Chilcote W A. Quantitaive analysis of breast parenchymal density: correlation with a women's age. Academic Radiology 1999; 6:742-747.

Priebe C E, Lorey R A, Marchette D J, Solka J L, Rogers G W. Nonparametric spatio-temporal change point analysis for early detection in mammography. Proceedings of the Second International Workshop on Digital Mammography, York England July 10-12 1994.

Raafat A M, Songjiang L i, Bennett J M, Hofseth L J, Haslam S Z. Estrogen and Estrogen Plus Progestin Act Directly on the Mammary Gland to Increase Proliferation in a Postmenopausal Mouse Model. Journal of Cellular Physiology 2001; 187:81-89.

Reichenbach J R, Przetak C, Klinger G, Kaiser W A. Assessment of breast tissue changes on hormonal replacement therapy using MRI: a pilot study. Journal of Computer Assisted Tomography 1999; 23:407-413.

Reid S E, Murthy M S, Kaufman M, Scanlon E F. Endocrine and paracrine hormones in the promotion, progression and recurrence of breast cancer. British Journal of Surgery 1996; 83:1037-1046.

Rideout D F, Poon P Y. Patterns of breast parenchyma on mammography. Journal of the Canadian Association of Radiologists 1977; 28:257-258.

Rockhill B, Colditz G A, Rosner B. Bias in breast cancer analysis due to error in age at menopause. American Journal of Epidemiology 2000; 151:404-408.

Rockhill B, Spiegelman D, Byrne C, Hunter D, Colditz G A. Validation of the Gail et al. Model of Breast Cancer Risk Prediction and Implications for Chemoprevention. Journal of the National Cancer Institute 2001; 93(5):358-366.

Roebuck E J. The importance of mammographic parenchymal patterns. The British Journal of Radiology 1982; 55:387-398.

Rosenberg R D, Hunt W C, Williamson M R, Gilliland F D, Wiest P W, Kelsey C A et al. Effects of age, breast density, ethnicity, and estrogen replacement therapy on screening mammographic sensitivity and cancer stage at diagnosis: review of 183, 134 screening mammograms in Albuquerque, N. Mex. Radiology 1998; 209:511-518.

Russo J, Hu Y F, Silva I D C G, Russo I H. Cancer Risk Related to Mammary Gland Structure and Development. Microscopy Research And Technique 52, 204-223. 2001.

Rutqvist L E, Miller A B, Andersson I, Hakama M, Hakulinen T, Sigfússon B F et al. Reduced breast-cancer mortality with mammography screening-an assessment of currently available data. International Journal of Cancer 1990; 5:76-84.

rutter C M, Mandelson M T, Laya M B, Seger D J, Taplin S. Changes in Breast Density Associated with Initiation, Discontinuation, and Continuing Use of Hormone Replacement Therapy. Journal of the American Medical Association 2001; 285(2):171-176.

Saarenmaa I, Salminen T, Geiger U, Holli K, Isola J, Kärkkäinen A et al. The visibility of cancer on earlier mammograms in a population-based screening programme. European Journal of Cancer 1999; 35:1118-1122.

Saftlas A F, Hoover R N, Brinton L A, Szklo M, Olson D R, Salane M et al. Mammographic densities and risk of breast cancer. Cancer 1991; 67:2833-2838.

Saftlas A F, Szklo M. Mammographic parenchymal patterns and breast cancer risk. Epidemiologic Reviews 1987; 9:146-174.

Saftlas A F, Wolfe J, Hoover R N, Brinton L A, Schairer C, Salane M et al. Mammographic parenchymal patterns as indicators of breast cancer risk. American Journal of Epidemiology 1989; 129:518-526.

Sala E, Solomon L, Warren R, McCann J, Duffy S, Luben R et al. Size, node status, and grade of breast tumours: association with mammographic parenchymal patterns. European Radiology 2000; 10:157-161.

Sala E, Warren R, Duffy S, Welch A, Luben R, Day N. High risk mammographic parenchymal patterns and diet: a case-control study. British Journal of Cancer 2000; 83:121-126.

Sala E, Warren R, McCann J, Duffy S, Day N, Luben R. Mammographic parenchymal patterns and mode of detection: implications for the breast screening programme. Journal of Medical Screening 1998; 5:207-212.

Sala E, Warren R, McCann J, Duffy S, Luben R, Day N. High-risk mammographic parenchymal patterns and anthropometric measures: a case-control study. British Journal of Cancer 1999; 81:1257-1261.

Salminen T, Hakama M, Heikkila M, Saarenmaa I. Favorable change in mammographic parenchymal patterns and breast cancer risk factors. International Journal of Cancer 1998; 78:410-414.

Salminen T M, Saarenmaa I E, Heikkilä M M, Hakama M. Is a Dense Mammographic Parenchymal Pattern a Contraindication to Hormone Replacement Therapy? Acta Oncologica 2000; 39(8):969-972.

Salminen T M, Saarenmaa I E, Heikkil a M M, Hakama M. Risk of breast cancer and changes in mammographic parenchymal patterns overtime. 1998; 37:547-551.

Salminen T M, Saarenmaa I E, Heikkil a M M, Hakama M. Unfavorable change in mammographic patterns and the breast cancer risk factors. Breast Cancer Research and Treatment 1999; 57:165-173.

Senie R T, Kinne D W. Menstrual timing of treatment for breast cancer. Monographs/National Cancer Institutes 1994; 16:85-90.

Singh A. Digital change detection techniques using remotely-sensed data. International Journal of Remote Sensing 1989; 10:989-1003.

Sivaramakrishna R, Obuchowski N A, Chilcote W A, Powell K A. Automatic Segmentation of Mammographic Density. Academic Radiology 2001; 8:250-256.

S ö derqvist G. Effects of sex steroids on proliferation in normal mammary tissue. Annals of Medicine 1998; 30:511-524.

Spicer D V, Krecker E A, Pike M C. The endocrine prevention of breast cancer. Cancer Investigations 1995; 13:495-504.

Spicer D V, Pike M C. Breast cancer prevention through modulation of endrogenous hormones. Breast Cancer Research and Treatment 1993; 28:179-193.

Spicer D V, Pike M C. Sex steroids and breast cancer prevention. Journal of the National Cancer Institute Monographs 1994; 16:139-147.

Spicer D V, Ursin G, Parisky Y R, Pearce J G, Shoupe D, Pike A et al. Changes in mammographic densities induced by a hormonal contraceptive designed to reduce breast cancer risk. Journal of the National Cancer Institute 1994; 86:431-436.

Spratt J S, Greenberg R A, Heuser L S. Geometry, growth rates, and duration of cancer and carcinoma in situ of the breast before detection by screening. Cancer Research 1986; 46:970-974.

Spratt J S, Heuser L, Kuhns J G, Reiman H M, Buchanan J B, Polk H C et al. Association between the actual doubling times of primary breast cancer with histopathologic characteristics and Wolfe's parenchymal mammographic patterns. Cancer 1981; 47:2265-2268.

Spratt J S. Re: Variation in mammographic breast density by time in menstrual cycle among women aged 40-49 years. Journal of the National Cancer Institute 1999; 91:90.

Stacey-Clear A, McCarthy K A, Hall D A, Pile-Spellman E, White G, Hulka C A et al. Mammographically detected breast cancer: location in women under 50 years old. Radiology 1993; 186:677-680.

Sterns E E, Zee B. Mammographic density changes in peri-menopausal and postmenopausal women: is effect of hormone replacement therapy predictable? Breast Cancer Research and Treatment 2000; 59:125-132.

Stomper P C, D'Souza D J D, DiNitto P A, Arredondo M A. Analysis of parenchymal density on mammograms in 1353 women 25-79 years old. American Journal of Roentgenology 1996; 167:1261-1265.

Stomper P C, Van Voorhis B J, Ravnikar V A, Meyer J E. Mammographic changes associated with postmenopausal hormone replacement therapy: a longitudinal study. Radiology 1990; 174:487-490.

Sylvester P A, Kutt E, Baird A, Vipond M N, Webb A J, Farndon J R. Rate and classification of interval cancers in the breast screening programme. Annals of the Royal College of Surgeons of England 1997; 79:276-277.

Tabar L, Dean P B. Mammographic parenchymal patterns. Risk indicator for breast cancer?Journal of the American Medical Association 1982; 247:185-189.

Tabar L, Fagerberg G, Chen H H, Duffy S W, Gad A. Tumour development, histology, and grade of breast cancers: prognosis and progression. International Journal of Cancer 1996; 66:413-419.

Tabar L, Vitak B, Chen H-H T, Yen M-F, Duffy S W, Smith R A. Beyond Randomized Controlled Trials Organized Mammographic Screening Substantially Reduces Breast Carcinoma Mortality. Cancer 2001; 91:1724-1731.

Tahoces P G, Correa J, Souto M, G ó mez L, Vidal J J. Computer assisted diagnosis: the classification of mammographic breast parenchymal patterns. Physics in Medicine and Biology 1995; 40:103-117.

Tavani A, Braga C, La Vecchia C, Parazzina F, Talamini R, Franceschi S. Height and Breast Cancer Risk. European Journal of Cancer 1998; 34(4):543-547.

Taylor P, Hajnal S, Dilhuydy M H, Barreau B. Measuring image texture to separate "difficult" from "easy" mammograms. The British Journal of Radiology 1994; 67:453-463.

Threatt B, Norbeck J M, Ullman N S, Kummer R, Roselle P. Association between mammographic parenchymal pattern classification and incidence of breast cancer. Cancer 1980; 45:2550-2556.

Thurfjell E, Hsieh C C, Lipworth L, Ekbom A, Adami H O, Trichopoulos D. Breast size and mammographic pattern in relation to breast cancer risk. European Journal of Cancer Prevention 1996; 5:37-41.

Thurfjell E L, Holmberg L H, Persson I R. Screening mammography: sensitivity and specificity in relation to hormone replacement therapy. Radiology 1997; 203:339-341.

Titus-Ernstoff L, Longnecker M P, Newcomb P A, Dain B, Greenberg E R, Mittendorf R et al. Menstrual factors in relation to breast cancer risk. Cancer Epidemiology Biomarkers and Prevention 1998; 7:783-789.

Turnbull A E, Kapera L, Cohen E L. Mammographic parenchymal patterns in Asian and Caucasian women attending for screening. Clinical Radiology 1993; 48:38-40.

Ursin G, Astrahan M A, Salane M, Parisky Y R, Pearce J G, Daniels J R et al. The detection of changes in mammographic densities. Cancer Epidemiology Biomarkers and Prevention 1998; 7:43-47.

Ursin G, Pike M C, Spicer D V, Porrath S A, Reitherman R W. Can mammographic densities predict effects of tamoxifen on the breast?Journal of the National Cancer Institute 1996; 88:128-129.

Vachon C M, Kushi L H, Cerhan J R, Kuni C C, Sellers T A. Association of diet and mammographic breast density in the Minnesota breast cancer family cohort. Cancer Epidemiology Biomarkers and Prevention 2000; 9:151-160.

van Dijck J A A M, Verbeek A L M, Hendriks J H C L, Holland R. The current detectability of breast cancer in a mammographic screening program. A review of the previous mammograms of interval and screen-detected cancers. Cancer 1993; 72:1933-1938.

van Gils C H, Hendriks J H, Otten J D, Holland R, Verbeek A L. Parity and Mammographic breast density in relation to breast cancer risk: indication of interaction. European Journal of Cancer Prevention 2000; 9(2):105-111.

van Gils C H, Hendriks J H C L, Holland R, Karssemeijer N, Otten J D M, Straatman H et al. Changes in mammographic breast density and concomitant changes in breast cancer risk. European Journal of Cancer Prevention 1999; 8:509-515.

van Gils C H, Otten J D M, Verbeek A L M, Hendriks J H C L. Mammographic breast density and risk of breast cancer: Masking bias or causality? European Journal of Epidemiology 1998; 14:315-320.

van Gils C H, Otten J D M, Verbeek A L M, Hendriks J H C L. Short communication: breast parenchymal patterns and their changes with age. The British Journal of Radiology 1995; 68:1133-1135.

van Gils C H. Mammographic density and breast cancer risk. European Journal of Obstetrics & Gynecology and Reproductive Biology 1999; 86:127-128.

van Hoften C, Burger H, Peeters P H M, Grobbee D E, van Noord P A H, Leufkens H G M. Long-term oral contraceptive use increases breast cancer risk in women over 55 years of age: the dom cohort. International journal of Cancer 2000; 87:591-594.

Verbeek A L M, Hendriks J H C L, Peeters P H M, Sturmans F. Mammographic breast pattern and the risk of breast cancer. The Lancet 1984; 1 (8377):591-593.

von Fournier D, Weber B, Hoeffken W, Bauer M, Kubli F, Barth V. Growth rate of 147 mammary carcinomas. Cancer 1980; 45:2198-2207.

von Rosen A, Frisell J, Nilsson R, Wiege M, Auer G. Histopathologic and cytochemical characteristics of interval breast carcinomas from Stockholm Mammography Screening Project. Acta Oncologica 1992; 31:399-402.

Warner E, Lockwood G, Math M, Tritchler D, Boyd N F. The risk of breast cancer associated with mammographic parenchymal patterns: a meta-analysis of the published literature to examine the effect of method of classification. Cancer Detection and Prevention 1992; 16:67-72.

Wazer D E, Gage I, Horner M J, Krosnick S H, Schmid C. Age-related differences in patients with nonpalpable breast carcinomas. Cancer 1996; 78:1432-1437.

Weich J, Adler O B. Breast pattern as a risk for development of cancer. Israel Journal of Medical Sciences 1981; 17:854-858.

Wellings S R, Wolfe J N. Correlative studies of the Histological and Radiographic Appearance of the Breast Parenchyma. Radiology 1978; 129:299-306.

White E, Malone K E, Weiss N S, Daling J R. Breast cancer among U.S. women in relation to oral contraceptive use. Journal of the National Cancer Institute 1994; 86:505-514.

White E, Velentgas P, Mandelson M T, Lehman C D, Elmore J G, Porter P et al. Variation in mammographic breast density by time in menstrual cycle among women aged 40-49 years. Journal of the National Cancer Institute 1998; 90:906-910.

White J. Breast density and cancer risk: what is the relationship?Journal of the National Cancer Institute 2000; 92:443.

Whitehead J, Carlile T, Kopecky K J, Thompson D J, Gilbert Jr F I, Present A J et al. Wolfe mammographic parenchymal patterns. A study of the masking hypothesis of Egan and Mosteller. Cancer 1985; 56:1280-1286.

Whitehead J, Carlile T, Kopecky K J, Thompson D J, Gilbert Jr F I, Present A J et al. The relationship between Wolfe's classification of mammograms, accepted breast cancer risk factors, and the incidence of breast cancer. American Journal of Epidemiology 1985; 122:994-1006.

Whitehouse G H, Leinster S J. The variation of breast parenchymal patterns with age. The British Journal of Radiology 1985; 58:315-318.

Wildes R P, Asmuth J C, Hunter D M, Kopans D B, Moore R H. Change Detection in Serial Mammograms for Early Detection of Breast Cancer. The National Information Display Laboratory, N1D L Report F R-0008, 1996. 1996.

Wilkinson E, Clopton C, Gordonson J, Green R, Hill A, Pike M C. Mammographic parenchymal pattern and risk of breast cancer. Journal of the National Cancer Institute 1977; 59:1397-1400.

Witt I, Hansen S, Brünner S. The risk of developing breast cancer in relation to mammography findings. European Journal of Radiology 1984; 4:65-67.

Wolfe J N, Albert S, Belle S, Salane M. Breast parenchymal patterns and their relationship to risk for having or developing carcinoma. Radiologic Clinics of North America 1983; 21:127-136.

Wolfe J N, Albert S, Belle S, Salane M. Familial influences on breast parenchymal patterns. Cancer 1980; 46:2433-2437.

Wolfe J N, Saftlas A F, Salane M. Mammographic parenchymal patterns and quantitative evaluation of mammographic densities: a case-control study. American Journal of Roentgenology 1987; 148:1087-1092.

Wolfe J N. A study of breast parenchyma by mammography in the normal woman and those with benign and malignant disease. Radiology 1967; 89:201-205.

Wolfe J N. Breast parenchymal patterns and their changes with age. Diagnostic Radiology 1976; 121:545-552.

Wolfe J N. Breast patterns as an index of risk for developing breast cancer. American Journal of Roentgenology 1976; 126:1130-1139.

Wolfe J N. Mammography: ducts as a sole indicator of breast carcinoma. Radiology 1967; 89:206-210.

Wolfe J N. Risk for breast cancer development determined by mammographic parenchymal pattern. Cancer 1976; 37:2486-2492.

Wolfe J N. Risk of developing breast cancer determined by mammography. Process in clinical and biological research. Breast Cancer 1977; 12:223-238.

Wolfe J N. The prominent duct pattern as an indicator of cancer risk. Oncology 1969; 23:149-158.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

The invention claimed is:

1. A computer implemented method of screening an asymptomatic patient's mammogram to detect abnormalities in the asymptomatic patient's mammogram, wherein screening the asymptomatic patient's mammogram to detect abnormalities is performed prior to classifying the detected abnormalities as being malignant or benign, the method of screening comprising:
    obtaining an asymptomatic patient's mammogram, the mammogram generated by a mammography machine;
    calculating a detection risk probability value associated with an asymptomatic patient, the detection risk probability value calculated from an array of risk factors associated with breast cancer;
    selecting a computer algorithm to detect abnormalities in the asymptomatic patient's mammogram;
    identifying a standard threshold of the computer algorithm for detecting false positive abnormalities, wherein the standard threshold is independent of the array of risk factors associated with the asymptomatic patient;
    adjusting the standard threshold of the computer algorithm for detecting false positive abnormalities in response to the detection risk probability value associated with the asymptomatic patient;
    detecting abnormalities in the asymptomatic patient's mammogram by applying the computer algorithm using the adjusted standard; and
    producing an electronic output image of the asymptomatic patient's mammogram that visualizes the detected abnormalities.

2. The method of claim 1 wherein the risk factors include relative risk values.

3. The method of claim 1 wherein the risk factors include odds ratio values.

4. The method of claim 1 wherein the risk factors include absolute risk values.

5. The method of claim 1 further comprising the steps of:
    obtaining a patient-specific breast tissue density value derived by automated means from the asymptomatic patient's mammogram; and
    integrating the breast tissue density value in the risk probability value.

6. The method of claim 1 further comprising the step of flagging the mammogram having detected abnormalities as generating a positive result for breast cancer requiring additional analysis.

7. The method of claim 1 further comprising the step of flagging the mammogram not having detected abnormalities as generating a negative result for breast cancer.

8. The method of claim 1 further comprising the steps of:
    providing a data entry interface adapted to input the array of risk factors associated with the patient;
    digitally acquiring the asymptomatic patient's mammogram; and
    applying the algorithm to the mammogram to detect abnormalities.

9. The method of claim 8 further comprising the step of storing the array of risk factors on an electronic storage medium communicatively coupled to the digitally acquired mammogram.

10. The method of claim 8 wherein the mammograms associated with abnormal risk findings are electronically presented with computer aided enhancement.

11. The method of claim 1 wherein the array of risk factors includes at least one factor selected from a group of factors including age, racial background, geographic background, hormonal data, breast size, weight and height, pregnancies, breast surgeries, breast water content, transverse relaxation time, family medical history, previous biopsies, length of reproductive years, menopausal status, parity, age of menarche, age of menopause, involution characterization, density time dependency, density dependent texture, dietary factors, abnormality spatial location and physical activity.

12. The method of claim 1, wherein the step of adjusting the standard threshold of the computer algorithm for detecting false positive abnormalities in response to the risk probability value associated with the asymptomatic patient further comprises:
    identifying an average value for the probability value;
    increasing the standard threshold if the probability value is higher than the average value; and
    decreasing the standard threshold if the probability value is lower than the average value.

13. A computer implemented method of screening an asymptomatic patient's mammogram to detect abnormalities in the asymptomatic patient's mammogram, wherein screening the asymptomatic patient's mammogram to detect abnormalities is performed prior to classifying the detected abnormalities as being malignant or benign, the method of screening comprising:
    obtaining an asymptomatic patient's mammogram, the mammogram generated by a mammography machine;
    identifying an average risk for breast cancer based on a set of risk factors;
    identifying an asymptomatic patient as being either at a high risk for breast or at a low risk for breast cancer based on the set of risk factors for breast cancer for the patient, wherein the patient is at a high risk for breast cancer if their risk is above the average risk and the patient is at a low risk for breast cancer if their risk is below the average risk;
    identifying a standard false positive detection threshold for the identification of abnormalities in a mammogram;
    adjusting the standard false positive detection threshold by increasing the standard false positive detection threshold if the asymptomatic patient is at a high risk for breast cancer and decreasing the standard false positive detection threshold if the patient is at a low risk for breast cancer;
    evaluating the asymptomatic patient's mammogram to detect abnormalities based on the adjusted false positive detection threshold; and
    producing an electronic output image of the asymptomatic patient's mammogram that visualizes the detected abnormalities.

* * * * *